United States Patent
Blake et al.

(10) Patent No.: US 11,274,284 B2
(45) Date of Patent: Mar. 15, 2022

(54) CELL-FREE PRODUCTION OF RIBONUCLEIC ACID

(71) Applicant: GreenLight Biosciences, Inc., Medford, MA (US)

(72) Inventors: William Jeremy Blake, Winchester, MA (US); Drew S. Cunningham, Winchester, MA (US); Daniel MacEachran, Medford, MA (US)

(73) Assignee: GreenLight Biosciences, Inc., Medford, MA (US)

( * ) Notice: Subject to any disclaimer, the term of this patent is extended or adjusted under 35 U.S.C. 154(b) by 93 days.

(21) Appl. No.: 15/562,456

(22) PCT Filed: Mar. 30, 2016

(86) PCT No.: PCT/US2016/024937
§ 371 (c)(1),
(2) Date: Sep. 28, 2017

(87) PCT Pub. No.: WO2016/160936
PCT Pub. Date: Oct. 6, 2016

(65) Prior Publication Data
US 2018/0087045 A1 Mar. 29, 2018

Related U.S. Application Data

(60) Provisional application No. 62/140,407, filed on Mar. 30, 2015.

(51) Int. Cl.
*C12N 9/22* (2006.01)
*C12N 1/20* (2006.01)
(Continued)

(52) U.S. Cl.
CPC ............ *C12N 9/22* (2013.01); *C12N 9/127* (2013.01); *C12N 9/1229* (2013.01); *C12N 9/1247* (2013.01); *C12N 15/09* (2013.01); *C07K 14/195* (2013.01); *C07K 2319/034* (2013.01); *C12N 1/06* (2013.01); *C12N 9/00* (2013.01);
(Continued)

(58) Field of Classification Search
CPC ............ C12N 9/22; C12N 15/10; C12P 19/30
See application file for complete search history.

(56) References Cited

U.S. PATENT DOCUMENTS 3,223,592 A 12/1965 Sakaguchi et al.
3,684,652 A 8/1972 Nakayama et al.
(Continued)

FOREIGN PATENT DOCUMENTS

CN 2563643 7/2003
CN 1329506 C 8/2007
(Continued)

OTHER PUBLICATIONS

Awano. *Escherichia coli* RNase R Has Dual Activities, Helicase and RNase. Journal of Bacteriology, Mar. 2010, p. 1344-1352.*
(Continued)

*Primary Examiner* — Yong D Pak
(74) *Attorney, Agent, or Firm* — Wolf, Greenfield & Sacks, P.C.

(57) ABSTRACT

Provided herein, in some aspects, are methods and compositions for cell-free production of ribonucleic acid.

24 Claims, 4 Drawing Sheets

Specification includes a Sequence Listing.

(51) Int. Cl.
    *C12N 15/09*   (2006.01)
    *C12N 9/12*    (2006.01)
    *C12N 1/06*    (2006.01)
    *C12N 9/00*    (2006.01)
    *C12N 15/10*   (2006.01)
    *C07K 14/195*  (2006.01)
    *C12N 15/63*   (2006.01)
    *C12P 19/30*   (2006.01)
    *C12P 19/34*   (2006.01)

(52) U.S. Cl.
    CPC .......... *C12N 15/10* (2013.01); *C12N 15/635* (2013.01); *C12N 2840/002* (2013.01); *C12P 19/30* (2013.01); *C12P 19/34* (2013.01)

(56) References Cited

U.S. PATENT DOCUMENTS

| | | |
|---|---|---|
| 3,950,357 A | 4/1976 | Kahan et al. |
| RE28,886 E | 6/1976 | Nakayama et al. |
| 4,006,060 A | 2/1977 | Kahan et al. |
| 4,194,047 A | 3/1980 | Christensen et al. |
| 4,248,966 A | 2/1981 | Demain et al. |
| 4,266,034 A | 5/1981 | Patel |
| 4,270,537 A | 6/1981 | Romaine |
| 4,292,436 A | 8/1981 | Liu et al. |
| 4,329,481 A | 5/1982 | Liu et al. |
| 4,374,772 A | 2/1983 | Hazen et al. |
| 4,438,201 A | 3/1984 | Kubo et al. |
| 4,458,066 A | 7/1984 | Caruthers et al. |
| 4,460,689 A | 7/1984 | Foor et al. |
| 4,596,556 A | 6/1986 | Morrow et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 4,946,783 A | 8/1990 | Beckwith et al. |
| 4,950,603 A | 8/1990 | Ingolia et al. |
| 5,000,000 A | 3/1991 | Ingram et al. |
| 5,001,055 A | 3/1991 | Imahori et al. |
| 5,015,235 A | 5/1991 | Man |
| 5,064,413 A | 11/1991 | McKinnon et al. |
| 5,070,020 A | 12/1991 | Ingolia et al. |
| 5,141,496 A | 8/1992 | Daito et al. |
| 5,190,521 A | 3/1993 | Hubbard et al. |
| 5,312,335 A | 5/1994 | McKinnon et al. |
| 5,319,122 A | 6/1994 | Friedman |
| 5,328,483 A | 7/1994 | Jacoby |
| 5,334,144 A | 8/1994 | Alchas et al. |
| 5,339,163 A | 8/1994 | Homma et al. |
| 5,417,662 A | 5/1995 | Hjertman et al. |
| 5,436,131 A | 7/1995 | Condra et al. |
| 5,466,220 A | 11/1995 | Brenneman |
| 5,383,851 A | 12/1995 | McKinnon et al. |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,593,856 A | 1/1997 | Choi et al. |
| 5,599,302 A | 2/1997 | Lilley et al. |
| 5,649,912 A | 7/1997 | Peterson |
| 5,665,566 A | 9/1997 | Lavaille |
| 5,672,497 A | 9/1997 | Cox et al. |
| 5,704,911 A | 1/1998 | Parsons |
| 5,871,922 A | 2/1999 | Salmond et al. |
| 5,893,397 A | 4/1999 | Peterson et al. |
| 5,993,412 A | 11/1999 | Deily et al. |
| 6,159,693 A | 12/2000 | Shultz et al. |
| 6,168,931 B1 | 1/2001 | Swartz et al. |
| 6,387,667 B1 | 5/2002 | Maruyama et al. |
| 6,440,688 B2 | 8/2002 | Bruce et al. |
| 6,472,169 B1 | 10/2002 | Frost et al. |
| 6,531,299 B1 | 3/2003 | Khosla et al. |
| 6,613,552 B1 | 9/2003 | Frost et al. |
| 6,746,859 B1 | 6/2004 | LaVallie |
| 6,921,659 B2 | 7/2005 | Joly |
| 6,994,986 B2 | 2/2006 | Swartz et al. |
| 7,041,479 B2 | 5/2006 | Swartz et al. |
| 7,223,390 B2 | 5/2007 | Brown |
| 7,226,767 B2 | 6/2007 | Maruyama et al. |
| 7,312,049 B2 | 12/2007 | Calhoun et al. |
| 7,338,789 B2 | 3/2008 | Swartz et al. |
| 7,341,852 B2 | 3/2008 | Voloshin et al. |
| 7,351,563 B2 | 4/2008 | Swartz et al. |
| 7,579,005 B2 | 8/2009 | Keeler et al. |
| 8,876,443 B2 | 7/2014 | Chan et al. |
| 8,859,247 B2 | 10/2014 | Koltermann et al. |
| 8,916,358 B2 | 12/2014 | Swartz |
| 8,956,833 B2 | 2/2015 | Swartz |
| 9,469,861 B2 | 10/2016 | Blake et al. |
| 9,611,487 B2 | 4/2017 | Blake et al. |
| 9,637,746 B2 | 5/2017 | Klein-Marcuschamer |
| 9,688,977 B2 | 6/2017 | Blake et al. |
| 10,036,001 B2 | 7/2018 | Swartz |
| 10,316,342 B2 | 6/2019 | MacEachran et al. |
| 10,421,953 B2 | 9/2019 | Blake et al. |
| 10,858,385 B2 | 12/2020 | Cunningham et al. |
| 10,954,541 B2 | 3/2021 | Blake et al. |
| 2002/0058303 A1 | 5/2002 | Swartz et al. |
| 2002/0127633 A1 | 9/2002 | Dilley et al. |
| 2002/0160459 A1 | 10/2002 | Berry et al. |
| 2003/0022178 A1 | 1/2003 | Schneewind et al. |
| 2003/0040086 A1 | 2/2003 | Dodge et al. |
| 2003/0113778 A1 | 6/2003 | Schulte et al. |
| 2004/0002103 A1 | 1/2004 | Short |
| 2004/0038250 A1 | 2/2004 | Nunez et al. |
| 2004/0091976 A1 | 5/2004 | Deng et al. |
| 2004/0209321 A1 | 10/2004 | Swartz et al. |
| 2005/0054044 A1 | 3/2005 | Swartz et al. |
| 2005/0239174 A1 | 10/2005 | Bao et al. |
| 2006/0234358 A1 | 10/2006 | Anderlei et al. |
| 2006/0281148 A1 | 12/2006 | Swartz et al. |
| 2007/0111283 A1 | 5/2007 | Cannon et al. |
| 2007/0154983 A1 | 7/2007 | Calhoun et al. |
| 2007/0161092 A1 | 7/2007 | Townsend et al. |
| 2007/0202198 A1 | 8/2007 | Purcell |
| 2008/0021205 A1 | 1/2008 | Blau et al. |
| 2008/0131925 A1 | 6/2008 | Berk et al. |
| 2009/0042244 A1 | 2/2009 | Voloshin et al. |
| 2009/0053779 A1 | 2/2009 | Lee et al. |
| 2009/0124012 A1 | 5/2009 | Nikolsky et al. |
| 2009/0155867 A1 | 6/2009 | Soucaille |
| 2009/0275096 A1 | 11/2009 | Burgard et al. |
| 2009/0275097 A1 | 11/2009 | Sun et al. |
| 2009/0312539 A1 | 12/2009 | Gnanaprakasam et al. |
| 2009/0325245 A1 | 12/2009 | Soucaille et al. |
| 2010/0120105 A1 | 5/2010 | Anthony et al. |
| 2010/0136640 A1 | 6/2010 | Lee et al. |
| 2010/0143997 A1 | 6/2010 | Buelter et al. |
| 2010/0291653 A1 | 11/2010 | Ness et al. |
| 2011/0008867 A1 | 1/2011 | Zarur et al. |
| 2011/0099670 A1 | 4/2011 | Koops et al. |
| 2011/0124069 A1 | 5/2011 | Mampel et al. |
| 2011/0262946 A1 | 10/2011 | Roy et al. |
| 2011/0269198 A1 | 11/2011 | Klein-Marcuschamer |
| 2011/0275116 A1 | 11/2011 | Swartz |
| 2011/0312052 A1 | 12/2011 | Koltermann et al. |
| 2012/0052547 A1 | 3/2012 | Swartz |
| 2012/0070870 A1 | 3/2012 | Way et al. |
| 2013/0065878 A1 | 3/2013 | Blake et al. |
| 2014/0193869 A1 | 7/2014 | Blake et al. |
| 2014/0271559 A1 | 9/2014 | Baum et al. |
| 2015/0037868 A1 | 2/2015 | Blake et al. |
| 2015/0064751 A1 | 3/2015 | Swartz |
| 2015/0191753 A1 | 7/2015 | Swartz |
| 2015/0337306 A1 | 11/2015 | Lieberman et al. |
| 2016/0028101 A1 | 1/2016 | Zhang et al. |
| 2016/0115558 A1 | 4/2016 | Swartz |
| 2017/0044554 A1 | 2/2017 | Zhang et al. |
| 2017/0096692 A1 | 4/2017 | Blake et al. |
| 2017/0159058 A1 | 6/2017 | Blake et al. |
| 2017/0247724 A1 | 8/2017 | Klein-Marcuschamer |
| 2017/0253866 A1 | 9/2017 | Blake et al. |

(56) References Cited

U.S. PATENT DOCUMENTS

| | | |
|---|---|---|
| 2017/0292138 A1 | 10/2017 | Blake et al. |
| 2018/0030416 A1 | 2/2018 | Pavez et al. |
| 2018/0273985 A1 | 9/2018 | Blake et al. |
| 2018/0320210 A1 | 11/2018 | MacEachran et al. |
| 2019/0144489 A1 | 5/2019 | Cunningham et al. |

FOREIGN PATENT DOCUMENTS

| | | |
|---|---|---|
| CN | 105219822 | 1/2016 |
| EP | 0 377 295 A1 | 7/1990 |
| EP | 0 444 775 A1 | 9/1991 |
| EP | 0 553 821 A1 | 8/1993 |
| EP | 1261696 A1 | 12/2002 |
| EP | 1264894 A1 | 12/2002 |
| EP | 1 279 736 A1 | 1/2003 |
| EP | 1327679 A1 | 7/2003 |
| EP | 1 433 856 A1 | 6/2004 |
| EP | 1 502 956 A1 | 2/2005 |
| EP | 1 514 927 A1 | 3/2005 |
| EP | 1631675 A1 | 3/2006 |
| EP | 1 939 210 A1 | 7/2008 |
| EP | 1587947 B1 | 1/2010 |
| EP | 2 204 453 A1 | 7/2010 |
| EP | 2377928 A2 | 10/2011 |
| GB | 2 018 822 A | 10/1979 |
| JP | 58-129992 | 8/1983 |
| JP | S61-260895 A | 11/1986 |
| JP | S63-7788 A | 1/1988 |
| JP | H01-228473 A | 9/1989 |
| JP | H07-298893 A | 11/1995 |
| JP | H08-502176 A | 3/1996 |
| JP | H08-196284 A | 8/1996 |
| JP | H10-500849 A | 1/1998 |
| JP | 2002-535008 A | 10/2002 |
| JP | 2003-517837 | 6/2003 |
| JP | 2005-160446 A2 | 6/2005 |
| JP | 05-176757 A2 | 7/2005 |
| JP | 2007-506430 | 3/2007 |
| JP | 2007-143463 A2 | 6/2007 |
| JP | 2007-521023 | 8/2007 |
| JP | 2007-534338 A | 11/2007 |
| JP | 2009-531050 A | 9/2009 |
| JP | 2013-021967 A | 2/2013 |
| JP | 2013-526277 A | 6/2013 |
| JP | 2013-537802 A | 10/2013 |
| JP | 5800218 B2 | 10/2015 |
| RU | 2169154 C2 | 6/2001 |
| RU | 2435862 C1 | 12/2011 |
| WO | WO 1995/032294 A1 | 11/1995 |
| WO | WO 1997/013537 A1 | 4/1997 |
| WO | WO 1997/037705 A1 | 10/1997 |
| WO | WO 1998/007690 A1 | 2/1998 |
| WO | WO 1999/034850 A1 | 7/1999 |
| WO | WO 99/50389 | 10/1999 |
| WO | WO 2000/003581 A1 | 1/2000 |
| WO | WO 2000/039288 A1 | 7/2000 |
| WO | WO 2000/044923 A1 | 8/2000 |
| WO | WO 2000/055353 A1 | 9/2000 |
| WO | WO 2000/061768 A2 | 10/2000 |
| WO | WO 2003/038117 A2 | 5/2003 |
| WO | WO 2003/054792 A2 | 7/2003 |
| WO | WO 2005/030949 A1 | 4/2005 |
| WO | WO 2005/030995 A1 | 4/2005 |
| WO | WO 2005/052117 A2 | 6/2005 |
| WO | WO 2005/098048 A1 | 10/2005 |
| WO | WO 2006/001382 A1 | 1/2006 |
| WO | WO 2006/090385 A2 | 8/2006 |
| WO | WO 2006/109751 A1 | 10/2006 |
| WO | WO 2007/053655 A2 | 5/2007 |
| WO | WO 2007/110619 A1 | 10/2007 |
| WO | WO 2007/137144 A2 | 11/2007 |
| WO | WO 2008/002661 A2 | 1/2008 |
| WO | WO 2008/002663 A2 | 1/2008 |
| WO | WO 2008/002673 A2 | 1/2008 |
| WO | WO 2008/066583 A2 | 6/2008 |
| WO | WO 2008/088884 A2 | 7/2008 |
| WO | WO 2008/094546 A2 | 8/2008 |
| WO | WO 2010/046713 A2 | 4/2010 |
| WO | WO 2010/074760 A1 | 7/2010 |
| WO | WO 2010/077806 A1 | 7/2010 |
| WO | WO 2011/017560 A1 | 2/2011 |
| WO | WO 2011/072287 A2 | 6/2011 |
| WO | WO 2011/140516 A2 | 11/2011 |
| WO | WO 2012/030980 A1 | 3/2012 |
| WO | WO 2012/135902 A1 | 10/2012 |
| WO | WO 2014/151190 A1 | 9/2014 |
| WO | WO 2014/197655 A1 | 12/2014 |
| WO | WO 2014/197702 A1 | 12/2014 |
| WO | WO 2015/021058 A2 | 2/2015 |
| WO | WO 2016/160936 A1 | 10/2016 |
| WO | WO 2017/176963 A1 | 10/2017 |
| WO | WO 2018/126287 A1 | 7/2018 |

OTHER PUBLICATIONS

Machine translation of JP 2013-526277.*
Partial Supplementary European Search Report for EP 16774076.0, dated Jan. 21, 2019.
Extended European Search Report for EP 16774076.0, dated Apr. 24, 2019.
International Preliminary Report on Patentability for PCT/US2017/026285, dated Oct. 18, 2018.
International Search Report and Written Opinion for PCT/US2018/055353, dated Jan. 7, 2019.
Arnold et al., Proteolytic degradation of ribonuclease A in the pretransition region of thermally and urea-induced unfolding. Eur J Biochem. Jan. 2001;268(1):93-7.
Hardy et al., Hepatitis C virus RNA synthesis in a cell-free system isolated from replicon-containing hepatoma cells. J Virol. Feb. 2003;77(3):2029-37.
Kuroda et al., Polyphosphate kinase as a nucleoside diphosphate kinase in *Escherichia coli* and Pseudomonas aeruginosa. Proc Natl Acad Sci USA. Jan. 21, 1997;94(2):439-442.
Motomura et al., A new subfamily of polyphosphate kinase 2 (class III PPK2) catalyzes both nucleoside monophosphate phosphorylation and nucleoside diphosphate phosphorylation. Appl Environ Microbiol. Apr. 2014;80(8):2602-8. doi: 10.1128/AEM.03971-13. Epub Feb. 14, 2014.
Ninh et al., Development of a continuous bioconversion system using a thermophilic whole-cell biocatalyst. Appl Environ Microbiol. Mar. 2013;79(6): 1996-2001. doi: 10.1128/AEM.03752-12. Epub Jan. 18, 2013.
U.S. Appl. No. 16/196,059, filed Nov. 20, 2018, Cunningham et al.
EP 16774076.0, Jan. 21, 2019, Partial Supplementary European Search Report.
EP 16774076.0, Apr. 24, 2019, Extended European Search Report.
PCT/US2017/026285, Oct. 28, 2018, International Preliminary Report on Patentability.
PCT/US2018/055353, Jan. 7, 2019, International Search Report and Written Opinion.
U.S. Appl. No. 13/606,911, filed Sep. 7, 2012, Blake et al.
U.S. Appl. No. 15/291,943, filed Oct. 12, 2016, Blake et al.
U.S. Appl. No. 13/102,967, filed May 6, 2011, Swartz.
U.S. Appl. No. 13/223,042, filed Aug. 31, 2011, Swartz.
U.S. Appl. No. 14/542,074, filed Nov. 14, 2014, Swartz.
U.S. Appl. No. 13/132,721, filed Jul. 12, 2011, Klein-Marcuschamer.
U.S. Appl. No. 15/462,274, filed Mar. 17, 2017, Klein-Marcuschamer.
U.S. Appl. No. 14/137,524, filed Dec. 20, 2013, Blake et al.
U.S. Appl. No. 14/451,708, filed Feb. 17, 2017, Blake et al.
U.S. Appl. No. 14/451,708, filed Aug. 5, 2014, Blake et al.
U.S. Appl. No. 15/600,553, filed May 19, 2017, Blake et al.
U.S. Appl. No. 15/559,126, filed Sep. 18, 2017, Blake et al.
U.S. Appl. No. 15/480,617, filed Apr. 6, 2017, Blake et al.
PCT/US2012/054195, Jan. 30, 2013, Invitation to Pay Additional Fees.
PCT/US2012/054195, Apr. 12, 2013, International Search Report and Written Opinion.

(56) References Cited

OTHER PUBLICATIONS

PCT/US2012/054195, Mar. 20, 2014, International Preliminary Report on Patentability.
PCT/US2011/035639, Sep. 12, 2011, Invitation to Pay Additional Fees.
PCT/US2011/035639, Nov. 18, 2011, International Search Report and Written Opinion.
PCT/US2011/035639, Nov. 22, 2012, International Preliminary Report on Patentability.
EP 17163812.5, Jul. 12, 2017, Extended European Search Report.
PCT/US2011/049997, Dec. 13, 2011, International Search Report and Written Opinion.
PCT/US2011/049997, Mar. 14, 2013, International Preliminary Report on Patentability.
EP 09836804.6, Jun. 4, 2012, Extended European Search Report.
PCT/US2009/067841, Mar. 22, 2010, International Search Report and Written Opinion.
PCT/US2009/067841, Jun. 30, 2011, International Preliminary Report on Patentability.
EP 09835395.6, Mar. 16, 2016, Extended European Search Report.
PCT/US2009/006704, Mar. 3, 2010, International Search Report and Written Opinion.
PCT/US2009/006704, Jul. 7, 2011, International Preliminary Report on Patentability.
PCT/US2013/077238, Mar. 18, 2014, Invitation to Pay Additional Fees.
PCT/US2013/077238, May 19, 2014, International Search Report and Written Opinion.
PCT/US2013/077238, Jul. 2, 2015, International Preliminary Report on Patentability.
PCT/US2014/049805, Nov. 14, 2014, Invitation to Pay Additional Fees.
PCT/US2014/049805, Feb. 16, 2015, International Search Report and Written Opinion.
PCT/US2014/049805, Feb. 18, 2016, International Preliminary Report on Patentability.
EP 14807322.4, Jan. 2, 2017, Extended European Search Report.
PCT/US2014/041009, Sep. 10, 2014, International Search Report and Written Opinion.
PCT/US2014/041009, Dec. 17, 2015, International Preliminary Report on Patentability.
PCT/US2016/023173, Jul. 8, 2016, Invitation to Pay Additional Fees.
PCT/US2016/023173, Sep. 16, 2016, International Search Report and Written Opinion.
PCT/US2016/023173, Sep. 28, 2017, International Preliminary Report on Patentability.
PCT/US2016/024937, Sep. 9, 2016, International Search Report and Written Opinion.
PCT/US2016/024937, Oct. 12, 2017, International Preliminary Report on Patentability.
PCT/US2017/026285, Jul. 6, 2017, Invitation to Pay Additional Fees.
PCT/US2017/026285, Aug. 28, 2017, International Search Report and Written Opinion.
Invitation to Pay Additional Fees for PCT/US2012/054195 mailed Jan. 30, 2013.
International Search Report and Written Opinion for PCT/US2012/054195 dated Apr. 12, 2013.
International Preliminary Report on Patentability for PCT/US2012/054195 dated Mar. 20, 2014.
Invitation to Pay Additional Fees for PCT/US2011/035639 mailed Sep. 12, 2011.
International Search Report and Written Opinion for PCT/US2011/035639 dated Nov. 18, 2011.
International Preliminary Report on Patentability for PCT/US2011/035639 dated Nov. 22, 2012.
Extended European Search Report for EP 17163812.5 dated Jul. 12, 2017.
International Search Report and Written Opinion for PCT/US2011/049997 dated Dec. 13, 2011.
International Preliminary Report on Patentability for PCT/US2011/049997 dated Mar. 14, 2013.
Extended European Search Report for EP 09836804.6 dated Jun. 4, 2012.
International Search Report and Written Opinion for PCT/US2009/067841 dated Mar. 22, 2010.
International Preliminary Report on Patentability for PCT/US2009/067841 dated Jun. 30, 2011.
Extended European Search Report for EP09835395.6 dated Mar. 16, 2016.
International Search Report and Written Opinion for PCT/US2009/006704 dated Mar. 3, 2010.
International Preliminary Report on Patentabilityfor PCT/US2009/006704 dated Jul. 7, 2011.
Invitation to Pay Additional Fees for PCT/US2013/077238 mailed Mar. 18, 2014.
International Search Report and Written Opinion for PCT/US2013/077238 dated May 19, 2014.
International Preliminary Report on Patentability for PCT/US2013/077238 dated Jul. 2, 2015.
Invitation to Pay Additional Fees for PCT/US2014/049805, mailed Nov. 14, 2014.
International Search Report for PCT/US2014/049805, dated Feb. 16, 2015.
International Preliminary Report on Patentability for PCT/US2014/049805, dated Feb. 18, 2016.
Extended European Search Report for EP 14807322.4, dated Jan. 2, 2017.
International Search Report and Written Opinion for PCT/US2014/041009, dated Sep. 10, 2014.
International Preliminary Report on Patentability for PCT/US2014/041009, dated Dec. 17, 2015.
Invitation to Pay Additional Fees for PCT/US2016/023173, mailed Jul. 8, 2016.
International Search Report and Written Opinion for PCT/US2016/023173, dated Sep. 16, 2016.
International Preliminary Report on Patentability for PCT/US2016/023173, dated Sep. 28, 2017.
International Search Report and Written Opinion for PCT/US2016/024937, dated Sep. 9, 2016.
International Preliminary Report on Patentability for PCT/US2016/024937, dated Oct. 12, 2017.
Invitation to Pay Additional Fees for PCT/US2017/026285, mailed Jul. 6, 2017.
International Search Report and Written Opinion for PCT/US2017/026285, dated Aug. 28, 2017.
[No Author Listed] Biapenem. Drugs Fut. 1994;19(7):631-637.
[No Author Listed] Biolistic® Particle Delivery System Bibliography. Bio-Rad Technical Bulletin #1687. Bio-Rad Laboratories. 12 pages.
[No Author Listed] Crude Lysate. Wikipedia entry for Crude Lysate, http://en.wikipedia.org/wiki/Crude_lysate downloaded on Mar. 3, 2015. Page Last Modified on Nov. 3, 2013. 1 page.
GENBANK Accession No. AAC43119. Analysis of the *Escherichia coli* genome. IV. DNA sequence of the region from 89.2 to 92.8 minutes. Sep. 3, 1993. 4 pages. Last accessed Jul. 26, 2016.
GENBANK Submission; NIH/NCBI, Accession No. AAB59985; Ling et al., Sequence analysis identifies the proline dehydrogenase and delta 1-pyrroline-5-carboxylate dehydrogenase domains of the multifunctional *Escherichia coli* PutA protein. Nov. 24, 1994.
GENBANK Submission; NIH/NCBI, Accession No. AAC73225; Blattner et al., pyruvate dehydrogenase, decarboxylase component E1, thiamine triphosphate-binding [*Escherichia coli* str. K-12 substr. MG1655]. Sep. 1, 2011.
GENBANK Submission; NIH/NCBI, Accession No. AAC73226; Blattner et al., pyruvate dehydrogenase, dihydrolipoyltransacetylase component E2 [*Escherichia coli* str. K-12 substr. MG1655]. Sep. 1, 2011.
GENBANK Submission; NIH/NCBI, Accession No. AAC73296; Blattner et al., acetyl-CoA carboxylase, carboxytransferase, alpha subunit [*Escherichia coli* str. K-12 substr. MG1655]. Sep. 1, 2011.

(56) References Cited

OTHER PUBLICATIONS

GENBANK Submission; NIH/NCBI, Accession No. AAC73346; Blattner et al., gamma-glutamate kinase [*Escherichia coli* str. K-12 substr. MG1655]. Sep. 1, 2011.
GENBANK Submission; NIH/NCBI, Accession No. AAC73347; Blattner et al., gamma-glutamylphosphate reductase [*Escherichia coli* str. K-12 substr. MG1655]. Sep. 1, 2011.
GENBANK Submission; NIH/NCBI, Accession No. AAC73842; Blattner et al., phosphoglyceromutase 1 [*Escherichia coli* str. K-12 substr. MG1655]. Sep. 1, 2011.
GENBANK Submission; NIH/NCBI, Accession No. AAC73957; Blattner et al., L-allo-threonine aldolase, PLP-dependent [*Escherichia coli* str. K-12 substr. MG 1655]. Sep. 1, 2011.
GENBANK Submission; NIH/NCBI, Accession No. AAC74746; Blattner et al., pyruvate kinase I [*Escherichia coli* str. K-12 substr. MG1655]. Sep. 1, 2011.
GENBANK Submission; NIH/NCBI, Accession No. AAC74849; Blattner et al., glyceraldehyde-3-phosphate dehydrogenase A [*Escherichia coli* str. K-12 substr. MG1655]. Sep. 1, 2011.
GENBANK Submission; NIH/NCBI, Accession No. AAC74924; Blattner et al., pyruvate kinase II [*Escherichia coli* str. K-12 substr. MG1655]. Sep. 1, 2011.
GENBANK Submission; NIH/NCBI, Accession No. AAC75447; Blattner et al., glucokinase [*Escherichia coli* str. K-12 substr. MG1655]. Sep. 1, 2011.
GENBANK Submission; NIH/NCBI, Accession No. AAC75821; Blattner et al., enolase [*Escherichia coli* str. K-12 substr. MG1655]. Sep. 1, 2011.
GENBANK Submission; NIH/NCBI, Accession No. AAC75962; Blattner et al., fructose-bisphosphate aldolase, class II [*Escherichia coli* str. K-12 substr. MG1655]. Sep. 1, 2011.
GENBANK Submission; NIH/NCBI, Accession No. AAC75963; Blattner et al., phosphoglycerate kinase [*Escherichia coli* str. K-12 substr. MG1655]. Sep. 1, 2011.
GENBANK Submission; NIH/NCBI, Accession No. AAC76849; Blattner et al., fused 3-hydroxybutyryl-CoA epimerase/delta(3)-cis-delta(2)-trans-enoyl-CoA isomerase/enoyl-CoA hydratase/3-hydroxyacyl-CoA dehydrogenase [*Escherichia coli* str. K-12 substr. MG1655]. Sep. 1, 2011.
GENBANK Submission; NIH/NCBI, Accession No. AAC76898; Blattner et al.; Sep. 1, 2011.
GENBANK Submission; NIH/NCBI, Accession No. AAC76901; Blattner et al., triosephosphate isomerase [*Escherichia coli* str. K-12 substr. MG1655]. Sep. 1, 2011.
GENBANK Submission; NIH/NCBI, Accession No. AAC76995; Blattner et al., glucosephosphate isomerase [*Escherichia coli* str. K-12 substr. MG1655]. Sep. 1, 2011.
GENBANK Submission; NIH/NCBI, Accession No. AAD38229; McGowan et al., CarA [*Pectobacterium carotovorum*]. Jul. 14, 1999.
GENBANK Submission; NIH/NCBI, Accession No. AAD38230; McGowan et al., CarB [*Pectobacterium carotovorum*]. Jul. 14, 1999.
GENBANK Submission; NIH/NCBI, Accession No. AAD38231; McGowan et al., CarC [*Pectobacterium carotovorum*]. Jul. 14, 1999.
GENBANK Submission; NIH/NCBI, Accession No. ABA79923; Copeland et al., acetyl-CoA acetyltransferase [Rhodobacter sphaeroides 2.4.1]. Nov. 21, 2011.
GENBANK Submission; NIH/NCBI, Accession No. ACJ71669; Erb et al., crotonyl-CoA carboxylase/reductase, partial [Rhodobacter sphaeroides]. Dec. 10, 2008.
GENBANK Submission; NIH/NCBI, Accession No. AEW99093; Ou et al., putative methyltransferase (plasmid) [Streptomyces cattleya NRRL 8057=DSM 46488]. Dec. 29, 2011.
GENBANK Submission; NIH/NCBI, Accession No. AEW99097; Ou et al., putative methyltransferase (plasmid) [Streptomyces cattleya NRRL 8057=DSM 46488]. Dec. 29, 2011.
GENBANK Submission; NIH/NCBI, Accession No. AEW99098; Ou et al., putative methyltransferase (plasmid) [Streptomyces cattleya NRRL 8057=DSM 46488]. Dec. 29, 2011.
GENBANK Submission; NIH/NCBI, Accession No. BAA22406; Mori et al., L-proline 3-hydroxylase [Streptomyces sp.]. Sep. 20, 1997.
GENBANK Submission; NIH/NCBI, Accession No. BAB67276; Kawarabayasi et al., malonyl-CoA/succinyl-CoA reductase [Sulfolobus tokodaii str. 7]. Aug. 17, 2011.
GENBANK Submission; NIH/NCBI, Accession No. CAD18973; Nunez et al., enoyl-CoA hydratase carB homologue [Streptomyces cattleya]. Apr. 15, 2005.
GENBANK Submission; NIH/NCBI, Accession No. CAD18975; Nunez et al., putative hydroxylase [Streptomyces cattleya]. Apr. 15, 2005.
GENBANK Submission; NIH/NCBI, Accession No. CAD18981; Nunez et al., putative beta-lactam synthetase [Streptomyces cattleya]. Apr. 15, 2005.
GENBANK Submission; NIH/NCBI, Accession No. CAD18985; Nunez et al., putative oxigenase [Streptomyces cattleya]. Apr. 15, 2005.
GENBANK Submission; NIH/NCBI, Accession No. CAD18990; Nunez et al., putative cysteine transferase [Streptomyces cattleya]. Apr. 15, 2005.
UniProtKB/Swiss-Prot; Accession No. P28269; Yonaha et al., The primary structure of omega-amino acid:pyruvate aminotransferase. Jul. 11, 2012.
Adams et al., Hindered dialkylamino nucleoside phosphite reagents in the synthesis of two DNA 51-mers. J Am Chem Soc. 1983;105(3):661-3.
Alber et al., Malonyl-coenzyme A reductase in the modified 3-hydroxypropionate cycle for autotrophic carbon fixation in archaeal Metallosphaera and Sulfolobus spp. J Bacteriol. Dec. 2006;188(24):8551-9. Epub Oct. 13, 2006.
Allain, Cell-free ethanol production: the future of fuel ethanol? J Chem Technol Biotechnol. 2007;82:117-20.
Alper et al., Tuning genetic control through promoter engineering. Proc Natl Acad Sci U S A. Sep. 6, 2005;102(36):12678-83. Epub Aug. 25, 2005.
Alves-Pereira et al., CDP-alcohol hydrolase, a very efficient activity of the 5'-nucleotidase/udp-sugar hydrolase encoded by the usha gene of yersinia intermedia and *escherichia coli*. J Bacteriol. Sep. 15, 2008;190(18):6153-61. Published ahead of print Jul. 18, 2008 , doi: 10.1128/JB.00658-08.
Anthony et al., Optimization of the mevalonate-based isoprenoid biosynthetic pathway in *Escherichia coli* for production of the anti-malarial drug precursor amorpha-4,11-diene. Metab Eng. Jan. 2009;11(1):13-9. Epub Aug. 12, 2008.
Atsumi et al., Acetolactate synthase from Bacillus subtilis serves as a 2-ketoisovalerate decarboxylase for isobutanol biosynthesis in *Escherichia coli*. Appl. Environ. Microbial. 2009;75:6306-11.
Atsumi et al., Metabolic engineering of *Escherichia coli* for 1-butanol production. Metab Eng. Nov. 2008;10(6):305-11. Epub Sep. 14, 2007.
Atsumi et al., Non-fermentative pathways for synthesis of branched-chain higher alcohols as biofuels. Nature. Jan. 3, 2008;451(7174):86-9.
Baba et al., Construction of *Escherichia coli* K-12 in-frame, single-gene knockout mutants: the Keio collection. Mol Syst Biol. 2006;2:2006.0008. Epub Feb. 21, 2006.
Bastian et al. Engineered ketol-acid reductoisomerase and alcohol dehydrogenase enable anaerobic 2-methylpropan-1-ol production at theoretical yield in *Escherichia coli*. Metab. Eng. 2011;13:345-52.
Bateson et al., Olivanic acid analogues. Part 6. Biomimetic synthesis of (±)-PS-5, (±)-6-Epi-PS-5, and (±)-benzyl MM22381. J Chem Soc Perkin Trans 1. 1990;1793-1801.
Baum et al., beta-Galactosidase containing a human immunodeficiency virus protease cleavage site is cleaved and inactivated by human immunodeficiency virus protease. Proc Natl Acad Sci U S A. Dec. 1990;87(24):10023-7.
Beaucage et al., Deoxynucleoside phosphoramidites—A new class of key intermediates for deoxypolynucleotide synthesis. Tetra Lett. 1981;22(20):1859-62.

(56) References Cited

OTHER PUBLICATIONS

Belousov et al., Sequence-specific targeting and covalent modification of human genomic DNA. Nucleic Acids Res. Sep. 1, 1997;25(17):3440-4.
Benton et al., Screening lambdagt recombinant clones by hybridization to single plaques in situ. Science. Apr. 8, 1977;196(4286):180-2.
Berge et al., Pharmaceutical salts. J Pharmaceut Sci. Jan. 1977;66(1):1-19.
Blattner et al., Analysis of the *Escherichia coli* genome. IV. DNA sequence of the region from 89.2 to 92.8 minutes. Nucleic Acids Res. Nov. 25, 1993;21(23):5408-17.
Blommers et al., Effects of the introduction of L-nucleotides into DNA. Solution structure of the heterochiral duplex d(G-C-G-(L)T-G-C-G).d(C-G-C-A-C-G-C) studied by NMR spectroscopy. Biochemistry. Jun. 28, 1994;33(25):7886-96.
Bodner et al., Definition of the common and divergent steps in carbapenem β-lactam antibiotic biosynthesis. Chembiochem. Sep. 19, 2011;12(14):2159-65. doi: 10.1002/cbic.201100366. Epub Aug. 24, 2011.
Bodner et al., Non-heme iron oxygenases generate natural structural diversity in carbapenem antibiotics. J Am Chem Soc. Jan. 13, 2010;132(1): 12-3.
Boiteux et al., Design of glycolysis. Philos Trans R Soc Lond B Biol Sci. Jun. 26, 1981;293(1063):5-22.
Bongaerts et al., Metabolic engineering for microbial production of aromatic amino acids and derived compounds. Metab Eng. Oct. 2001;3(4):289-300.
Boyer et al., Cell-free synthesis and maturation of [FeFe] hydrogenases. Biotechnol Bioeng. Jan. 1, 2008;99(1):59-67.
Bradley, Star role for bacteria in controlling flu pandemic? Nat Rev Drug Discov. Dec. 2005;4(12):945-6.
Brady et al., Transfer of Pantoea citrea, Pantoea punctata and Pantoea terrea to the genus Tatumella emend. as Tatumella citrea comb. nov., Tatumella punctata comb. nov. and Tatumella terrea comb. nov. and description of Tatumella morbirosei sp. nov. Int J Syst Evol Microbiol. Mar. 2010;60(Pt 3):484-94. doi: 10.1099/ijs.0.012070-0. Epub Aug. 4, 2009.
Brown et al., Chemical synthesis and cloning of a tyrosine tRNA gene. Methods Enzymol. 1979;68:109-51.
Buist et al., Different subcellular locations of secretome components of Gram-positive bacteria. Microbiology. Oct. 2006;152(Pt 10):2867-74.
Bujara et al., Exploiting cell-free systems: Implementation and debugging of a system of bio transformations. Biotechnol Bioeng. Jun. 15, 2010;106(3):376-89. doi: 10.1002/bit.22666.
Bujara et al., Optimization of a blueprint for in vitro glycolysis by metabolic real-time analysis. Nat Chem Biol. May 2011;7(5):271-7. doi: 10.1038/nchembio.541. Epub Mar. 20, 2011.
Calhoun et al., An economical method for cell-free protein synthesis using glucose and nucleoside monophosphates. Biotechnol Prog. Jul.-Aug. 2005;21(4): 1146-53.
Calhoun et al., Energizing cell-free protein synthesis with glucose metabolism. Biotechnol Bioeng. Jun. 5, 2005;90(5):606-13.
Calhoun et al., Energy systems for ATP regeneration in cell-free protein synthesis reactions. Methods in Molecular Biology. In vitro transcription and translation protocols. 2007;375(2):3-17.
Calhoun et al., Total amino acid stabilization during cell-free protein synthesis reactions. J Biotechnol. May 17, 2006;123(2):193-203. Epub Jan. 26, 2006.
Campbell et al., The CTP:phosphocholine cytidylyltransferase encoded by the licC gene of *Streptococcus pneumoniae*: cloning, expression, purification, and characterization. Biochim Biophys Acta. Dec. 30, 2001;1534(2-3):85-95.
Chandran et al., Phosphoenolpyruvate availability and the biosynthesis of shikimic acid. Biotechnol Prog. May-Jun. 2003;19(3):808-14.
Chang et al., YPA: an integrated repository of promoter features in *Saccharomyces cerevisiae*. Nucleic Acids Res. Jan. 2011;39(Database issue):D647-52. Epub Nov. 2, 2010.
Chen et al., A modified osmotic shock for periplasmic release of a recombinant creatinase from *Escherichia coli*. Biochem Eng J. 2004;19:211-5.
Chen et al., Crystal structures of penicillin-binding protein 6 from *Escherichia coli*. J Am Chem Soc. Oct. 14, 2009;131(40):14345-54.
Chen et al., High-level accumulation of a recombinant antibody fragment in the periplasm of *Escherichia coli* requires a triple-mutant (degP prc spr) host strain. Biotechnol Bioeng. Mar. 5, 2004;85(5):463-74.
Cheng et al., Purification and characterization of the *Escherichia coli* exoribonuclease RNase R. Comparison with RNase II. J Biol Chem. Jun. 14, 2002;277(24):21624-9. Epub Apr. 10, 2002.
Chisti et al., Disruption of microbial cells for intracellular products. Enzyme Micro Technol 1986;8(4): 194-204. doi 10.1016/0141-0229(86)90087-6.
Chiu et al., Site-directed, Ligase-Independent Mutagenesis (SLIM): a single-tube methodology approaching 100% efficiency in 4 h. Nucleic Acids Res. Dec. 7, 2004;32(21):e174.
Chong et al., Single-column purification of free recombinant proteins using a self-cleavable affinity tag derived from a protein splicing element. Gene. Jun. 19, 1997;192(2):271-81.
Choubey et al., Molecular characterization and localization of Plasmodium falciparum choline kinase. Biochim Biophys Acta. Jul. 2006;1760(7):1027-38.
Collins-Racie et al., Production of recombinant bovine enterokinase catalytic subunit in *Escherichia coli* using the novel secretory fusion partner DsbA. Biotechnology (N Y). Sep. 1995;13(9):982-7.
Coulthurst et al., Regulation and biosynthesis of carbapenem antibiotics in bacteria. Nat Rev Microbiol. Apr. 2005;3(4):295-306. Erratum included.
Dahiyat et al., De novo protein design: fully automated sequence selection. Science. Oct. 3, 1997;278(5335):82-7.
Dahl et al., Isolation and characterization of Chinese hamster ovary cells defective in the intracellular metabolism of low density lipoprotein-derived cholesterol. J Biol Chem. Mar. 5, 1992;267(7):4889-96.
Dancz et al., Inducible control of virulence gene expression in Listeria monocytogenes: temporal requirement of listeriolysin 0 during intracellular infection. J Bacteriol. Nov. 2002;184(21):5935-45.
Danese et al., Targeting and assembly of periplasmic and outer-membrane proteins in *Escherichia coli*. Annu Rev Genet. 1998;32:59-94.
Dani et al., Isolation and characterization of a thylakoid membrane module showing partial light and dark reactions. Biochim Biophys Acta. May 15, 2005;1669(1):43-52.
Daniell et al., Transformation of the cyanobacterium Anacystis nidulans 6301 with the *Escherichia coli* plasmid pBR322. Proc Natl Acad Sci U S A. Apr. 1986;83(8):2546-50.
Datsenko et al., One-step inactivation of chromosomal genes in *Escherichia coli* K-12 using PCR products. Proc Natl Acad Sci U S A. Jun. 6, 2000;97(12):6640-5.
Daube et al., Cell-free co-synthesis of protein nanoassemblies: tubes, rings, and doughnuts. Nano Lett. Mar. 2007;7(3):638-41. Epub Feb. 2, 2007.
De Boer et al., Protein targeting towards the thylakoid lumen of chloroplasts: proper localization of fusion proteins is only observed in vivo. EMBO J. Oct. 1991;10(10):2765-72.
De La Plaza et al., Biochemical and molecular characterization of alpha-ketoisovalerate decarboxylase, an enzyme involved in the formation of aldehydes from amino acids by Lactococcus lactis. FEMS Microbial. Lett. 2004;238:367-374.
De Mey et al., Construction and model-based analysis of a promoter library for *E. coli*: an indispensable tool for metabolic engineering. BMC Biotechnol. Jun. 18, 2007;7:34.
De Vries et al., Cloning, expression, and sequence analysis of the Bacillus methanolicus C1 methanol dehydrogenase gene. J Bacteriol. Aug. 1992;174(16):5346-53.
Dietrich et al., A novel semi-biosynthetic route for artemisinin production using engineered substrate-promiscuous P450(BM3). ACS Chem Biol. Apr. 17, 2009;4(4):261-7.

(56) References Cited

OTHER PUBLICATIONS

Ding et al., Functional analysis of the essential bifunctional tobacco enzyme 3-dehydroquinate dehydratase/shikimate dehydrogenase in transgenic tobacco plants. J Exp Bot. 2007;58(8):2053-67. Epub Apr. 26, 2007.
Dingwall et al., The nucleoplasmin nuclear location sequence is larger and more complex than that of SV-40 large T antigen. J Cell Biol. Sep. 1988;107(3):841-9.
Draper et al., Ti plasmid homologous sequences present in tissues from agrobacterium plasmid-transformed petunia protoplasts. Plant Cell Physiol. 1982;23(3):451-8.
Egan et al., Transketolase kinetics. The slow reconstitution of the holoenzyme is due to rate-limiting dimerization of the subunits. J Biol Chem. May 25, 1981;256(10):4877-83.
Ehrmann et al., TnTIN and TnTAP: mini-transposons for site-specific proteolysis in vivo. Proc Natl Acad Sci U S A. Nov. 25, 1997;94(24):13111-5.
Elander, Industrial production of beta-lactam antibiotics. Appl Microbiol Biotechnol. Jun. 2003;61(5-6):385-92. Epub Apr. 3, 2003.
Ellermeier et al., Construction of targeted single copy lac fusions using lambda Red and FLP-mediated site-specific recombination in bacteria. Gene. May 15, 2002;290(1-2):153-61.
Endoh et al., Cell-free protein synthesis at high temperatures using the lysate of a hyperthermophile. J Biotechnol. Nov. 1, 2006;126(2):186-95. Epub May 30, 2006.
Erb et al., Carboxylation mechanism and stereochemistry of crotonyl-CoA carboxylase/reductase, a carboxylating enoyl-thioester reductase. Proc Natl Acad Sci U S A. Jun. 2, 2009;106(22):8871-6. Epub May 20, 2009.
Erb et al., Synthesis of C5-dicarboxylic acids from C2-units involving crotonyl-CoA carboxylase/reductase: The ethylmalonyl-CoA pathway. Proc Nat Acad Sci. Jun. 4, 2007;104(25):10631-6.
Eser et al.,Target-directed proteolysis in vivo. Methods Enzymol. 2007;421:68-83.
Evans et al., The asymmetric synthesis of β-lactam antibiotics—IV. A formal synthesis of thienamycin. Tetra Lett. 1986;27(41):4961-4.
Fischer et al., Metabolic flux profiling of *Escherichia coli* mutants in central carbon metabolism using GC-MS. Eur J Biochem. Mar. 2003;270(5):880-91.
Flores et al., Pathway engineering for the production of aromatic compounds in *Escherichia coli*. Nat Biotechnol. May 1996;14(5):620-3.
Flores et al., Analysis of carbon metabolism in *Escherichia coli* strains with an inactive phosphotransferase system by (13)C labeling and NMR spectroscopy. Metab Eng. Apr. 2002;4(2):124-37.
Flores et al., Growth-rate recovery of *Escherichia coli* cultures carrying a multicopy plasmid, by engineering of the pentose-phosphate pathway. Biotechnol Bioeng. Aug. 20, 2004;87(4):485-94.
Fox et al., Methane monooxygenase from Methylosinus trichosporium OB3b. Purification and properties of a three-component system with high specific activity from a type II methanotroph. J Biol Chem. Jun. 15, 1989;264(17):10023-33.
Fradejas et al., The control of shikimic acid synthesis by tyrosine and phenylalamine. Biochem Biophys Res Commun. Jul. 26, 1961;5:320-3.
Freeman et al., Four enzymes define the incorporation of coenzyme A in thienamycin biosynthesis. Proc Natl Acad Sci U S A. Aug. 12, 2008;105(32): 11128-33. Epub Aug. 4, 2008. Supplemental material included.
Freeman et al., A comparison of methods for plasmid delivery into plant protoplasts. Plant Cell Physiol. 1984;25(8):1353-65.
Frenkel et al., 7,12-dimethylbenz[a]anthracene induces oxidative DNA modification in vivo. Free Radic Biol Med. Sep. 1995;19(3):373-80.
Friesen et al., Purification and Kinetic Characterization of CTP: Phosphocholine Cytidylyltransferase from *Saccharomyces cerevisiae*. Protein Expression and Purification. Feb. 2001;21(1):141-8.
Fujio et al., Construction of a plasmid carrying both CTP synthetase and a fused gene formed from cholinephosphate cytidylyltransferase and choline kinase genes and its application to industrial CDP-choline production: enzymatic production of CDP-choline from orotic acid (Part II). Biosci Biotechnol Biochem. Jun. 1997;61(6):960-4.
Fujio et al., Production of ATP from Adenine by Brevibacterium ammoniagenes, J Ferment Technol. 1983;61(3):261-267.
Gaspar et al., High yields of 2,3-butanediol and mannitol in Lactococcus lactis through engineering of $NAD^+$ cofactor recycling. Appl Environ Microbiol. Oct. 2011;77(19):6826-35. Epub Aug. 12, 2011. Supplemental material included.
Ger et al., A single Ser-180 mutation desensitizes feedback inhibition of the phenylalanine-sensitive3-deoxy-D-arabino-heptulosonate 7-phosphate (DAHP) synthetase in *Escherichia coli*. J Biochem. Nov. 1994;116(5):986-90.
Gibellini et al., Biochemical characterization of the initial steps of the Kennedy pathway in Trypanosoma brucei: the ethanolamine and choline kinases. Biochem J. 2008;415:135-44. Supplemental material included.
Goerke et al., Cell-free metabolic engineering promotes high-level production of bioactive Gaussia princeps luciferase.Metab Eng. May-Jul. 2008;10(3-4):187-200. doi: 10.1016/j.ymben.2008.04. 001. Epub May 2, 2008.
Goerke et al., Development of cell-free protein synthesis platforms for disulfide bonded proteins. Biotechnol Bioeng. Feb. 1, 2008;99(2):351-67. Epub Jul. 11, 2007.
Goody, A simple and rapid method for the synthesis of nucleoside 5'-monophosphates enriched with 17O or 18O on the phosphate group. Anal Biochem. Jan. 15, 1982;119(2):322-4.
Gordon-Kamm et al., Transformation of Maize Cells and Regeneration of Fertile Transgenic Plants. Plant Cell. Jul. 1990;2(7):603-618.
Gosset et al., A direct comparison of approaches for increasing carbon flow to aromatic biosynthesis in *Escherichia coli*. J Ind Microbiol. Jul. 1996;17(1):47-52.
Grabowski, Enantiopure drug synthesis: from methyldopa to imipenem to efavirenz. Chirality. 2005; 17 Suppl:S249-59.
Grieco et al., β-Lactam antibiotics: a formal stereocontrolled total synthesis of (.+−.) thienamycin. J Am Chem Soc. 1984;106(21):6414-7.
Grunstein et al., Colony hybridization: a method for the isolation of cloned DNAs that contain a specific gene. Proc Natl Acad Sci U S A. Oct. 1975;72(10):3961-5.
Hamed et al., Carboxymethylproline synthase catalysed syntheses of functionalized N-heterocycles. Chem Commun (Camb). Mar. 7, 2010;46(9): 1413-5. Epub Jan. 12, 2010.
Hamed et al., Crotonase catalysis enables flexible production of functionalized prolines and carbapenams. J Am Chem Soc. Jan. 11, 2012;134(1):471-9. doi: 10.1021/ja208318d. Epub Dec. 14, 2011.
Hamed et al., Evidence that thienamycin biosynthesis proceeds via C-5 epimerization: I catalyzes the formation of (2S,5S)-trans-carboxymethylproline. Chembiochem. Jan. 26, 2009;10(2):246-50.
Hamed et al., The enzymes of β-lactam biosynthesis. Nat Prod Rep. Jan. 2013;30(1):21-107. doi: 10.1039/c2np20065a.
Han et al., Paraffin oil as a "methane vector" for rapid and high cell density cultivation of Methylosinus trichosporium OB3b. Appl Microbiol Biotechnol. Jun. 2009;83(4):669-77. doi: 10.1007/s00253-009-1866-2. Epub Feb. 12, 2009.
Hawley et al., Compilation and analysis of *Escherichia coli* promoter DNA sequences. Nucleic Acids Res. Apr. 25, 1983;11(8):2237-55.
Herrmann, The shikimate pathway as an entry to aromatic secondary metabolism. Plant Physiol. Jan. 1995;107(1):7-12.
Hethke et al., Cell-free transcription at 95 degrees: thermostability of transcriptional components and DNA topology requirements of Pyrococcus transcription. Genetics. Aug. 1999;152(4):1325-33.
Hikita et al., Effects of total hydrophobicity and length of the hydrophobic domain of a signal peptide on in vitro translocation efficiency. J Biol Chem. 1992;267:4882-8.

(56) References Cited

OTHER PUBLICATIONS

Hikita et al., The requirement of a positive charge at the amino terminus can be compensated for by a longer central hydrophobic stretch in the functioning of signal peptides. J Biol Chem. 1992;267:12375-9.
Hodgson et al., π-Allyltricarbonyliron lactone complexes in synthesis: application to the synthesis of the β-lactam antibiotic (+)-thienamycin. J Chem Soc Chem Comm. 1984;8:494-6.
Horak et al., Two distinct proteolytic systems responsible for glucose-induced degradation of fructose-1,6-bisphosphatase and the Gal2p transporter in the yeast *Saccharomyces cerevisiae* share the same protein components of the glucose signaling pathway. J Biol Chem. Mar. 8, 2002;277(10):8248-54. Epub Dec. 28, 2001.
Hryniewicz et al., Sulfate and thiosulfate transport in Escherichia coli K-12: identification of a gene encoding a novel protein involved in thiosulfate binding. J Bacteriol. Jun. 1990;172(6):3358-66.
Inouye, The discovery of mRNA interferases: implication in bacterial physiology and application to biotechnology. J Cell Physiol. Dec. 2006;209(3):670-6.
Ishii et al., DBTBS: a database of Bacillus subtilis promoters and transcription factors. Nucleic Acids Res. Jan. 1, 2001;29(1):278-80.
Jacobi et al., Formal Total Syntheses of the β-Lactam Antibiotics Thienamycin and PS-5. J Org Chem. 1996;61(7):2413-27.
Jang et al., Sugar sensing in higher plants. Plant Cell. Nov. 1994;6(11): 1665-79.
Jenny et al., A critical review of the methods for cleavage of fusion proteins with thrombin and factor Xa. Protein Expr Purif. Sep. 2003;31(1):1-11.
Jermutus et al., Recent advances in producing and selecting functional proteins by using cell-free translation. Curr Opin Biotechnol. Oct. 1998;9(5):534-48.
Jewett et al., An integrated cell-free metabolic platform for protein production and synthetic biology. Mol Syst Biol. 2008;4:220. Epub Oct. 14, 2008.
Jewett et al., Mimicking the *Escherichia coli* cytoplasmic environment activates long-lived and efficient cell-free protein synthesis. Biotechnol Bioeng. Apr. 5, 2004;86(1): 19-26.
Jonnalagadda et al., Flux regulation in glycogen-induced oscillatory glycolysis in cell-free extracts of *Saccharomyces carlsbergensis*. Biosystems. 1982;15(1):49-58.
Kahan et al., Thienamycin, a new beta-lactam antibiotic. I. Discovery, taxonomy, isolation and physical properties. J Antibiot (Tokyo). Jan. 1979;32(1):1-12.
Kahan et al., Thienamycin: development of imipenen-cilastatin. J Antimicrob Chemother. Dec. 1983;12 Suppl D:1-35.
Kalderon et al., A short amino acid sequence able to specify nuclear location. Cell. Dec. 1984;39(3 Pt 2):499-509.
Kametani et al., Studies on the syntheses of heterocyclic compounds. 800. A formal total synthesis of (.+-.)-thienamycin and a (.+-.)-decysteaminylthienamycin derivative. J Am Chem Soc. 1980;102(6):2060-5.
Kang et al., Enhanced biodegradation of toxic organophosphate compounds using recombinant *Escherichia coli* with sec pathway-driven periplasmic secretion of organophosphorus hydrolase. Biotechnol Prog. Mar.-Apr. 2006;22(2):406-10.
Kapust et al., Tobacco etch virus protease: mechanism of autolysis and rational design of stable mutants with wild-type catalytic proficiency. Protein Eng. Dec. 2001;14(12):993-1000.
Kawarasaki et al., Prolonged cell-free protein synthesis in a batch system using wheat germ extract.Biosci Biotechnol Biochem. Oct. 1994;58(10):1911-3.
Kern et al., Engineering primary metabolic pathways of industrial micro-organisms. J Biotechnol. Mar. 30, 2007;129(1):6-29. Epub Dec. 2, 2006.
Kikuchi et al., Mutational analysis of the feedback sites of phenylalanine-sensitive 3-deoxy-D-arabino-heptulosonate-7-phosphate synthase of *Escherichia coli*. Appl Environ Microbiol. Feb. 1997;63(2):761-2.
Kim et al., Expression, purification, and characterization of choline kinase, product of the cki gene from *saccharomyces cerevisiae*. J Bio Chem. 1998;273(12):6844-6852.
Kim et al., Metabolic flux analysis for calcium dependent antibiotic (CDA) production in Streptomyces coelicolor. Metab Eng. Oct. 2004;6(4):313-25.
Kim et al., Prolonged cell-free protein synthesis using dual energy sources: Combined use of creatine phosphate and glucose for the efficient supply of ATP and retarded accumulation of phosphate. Biotechnol Bioeng. Aug. 15, 2007;97(6):1510-5.
Kim et al., Regeneration of adenosine triphosphate from glycolytic intermediates for cell-free protein synthesis.Biotechnol Bioeng. Aug. 20, 2001;74(4):309-16.
Kimmel, Identification and characterization of specific clones: strategy for confirming the validity of presumptive clones. Methods Enzymol. 1987;152:507-11.
Kindle, High-frequency nuclear transformation of Chlamydomonas reinhardtii. Proc Natl Acad Sci U S A. Feb. 1990;87(3):1228-32.
Klemme, Photoproduction of hydrogen by purple bacteria: A critical evaluation of the rate limiting enzymatic steps. J Bioscience 1993;48:482-87.
Klimov et al., New phelonic inhibitors of electron transfer in photosystem II. Biologichesksie Membrany. 1992;9(6):565-575.
Knapp et al., Cell-free production of active *E. coli* thioredoxin reductase and glutathione reductase. FEBS Lett. Feb. 13, 2004;559(1-3):66-70.
Knop et al., Hydroaromatic equilibration during biosynthesis of shikimic acid. J Am Chem Soc. Oct. 24, 2001;123(42):10173-82.
Ko et al., Targeting of proteins to the thylakoid lumen by the bipartite transit peptide of the 33 kd oxygen-evolving protein. EMBO J. Nov. 1989;8(11):3187-94.
Krämer et al., Metabolic engineering for microbial production of shikimic acid. Metab Eng. Oct. 2003;5(4):277-83.
Krell et al., Crystallization and preliminary X-ray crystallographic analysis of shikimate kinase from Erwinia chrysanthemi. Acta Crystallogr D Biol Crystallogr. Sep. 1, 1997;53(Pt 5):612-4.
Krutsakorn et al., In vitro production of n-butanol from glucose. Metab Eng. Nov. 2013;20:84-91. doi: 10.1016/j.ymben.2013.09. 006. Epub Sep. 19, 2013.
Kumagai et al., Current status of oral carbapenem development. Curr Med Chem—Anti-Infective Agents. Jan. 2002;1(1):1-14.
Kunkel, Rapid and efficient site-specific mutagenesis without phenotypic selection. Proc Natl Acad Sci U S A. Jan. 1985;82(2):488-92.
Lee et al., Fermentative production of thymidine by a metabolically engineered *Escherichia coli* strain. Appl Environ Microbiol. Apr. 2009;75(8):2423-32. Epub Feb. 27, 2009.
Lee et al., Systems metabolic engineering of *Escherichia coli* for L-threonine production. Mol Syst Biol. 2007;3:149. Epub Dec. 4, 2007.
Lee, High cell-density culture of *Escherichia coli*. Trends Biotechnol. Mar. 1996;14(3):98-105.
Li et al., Improved cell-free RNA and protein synthesis system. PLoS One. Sep. 2, 2014;9(9):e106232. doi: 10.1371/journal.pone. 0106232. eCollection 2014.
Li et al., Rational strain improvement for enhanced clavulanic acid production by genetic engineering of the glycolytic pathway in Streptomyces clavuligerus. Metab Eng. May 2006;8(3):240-52. Epub Mar. 10, 2006.
Liu et al., Combined biosynthetic pathway for de novo production of UDP-galactose: catalysis with multiple enzymes immobilized on agarose beads. Chembiochem. Apr. 2, 2002;3(4):348-55.
Liu et al., Streamlining *Escherichia coli* S30 extract preparation for economical cell-free protein synthesis. Biotechnol Prog. Mar.-Apr. 2005;21(2):460-5.
Ludwig et al., Mutations affecting export and activity of cytolysin A from *Escherichia coli*. J Bacteriol. Aug. 2010;192(15):4001-11. Epub May 28, 2010.
Luli et al., Comparison of growth, acetate production, and acetate inhibition of *Escherichia coli* strains in batch and fed-batch fermentations. Appl Environ Microbiol. Apr. 1990;56(4):1004-11.
Mackle et al., Role of signal peptides in targeting of proteins in cyanobacteria. J Bacteriol. Apr. 1994;176(7):1857-64.
Mandel et al., Modular synthesis of pantetheine and phosphopantetheine. Org Lett. Dec. 23, 2004;6(26):4801-3.

(56) References Cited

OTHER PUBLICATIONS

Martin et al., Engineering a mevalonate pathway in *Escherichia coli* for production of terpenoids. Nat Biotechnol. Jul. 2003;21(7):796-802. Epub Jun. 1, 2003.

Mayes, Metabolism of Glycogen. In: Harper's Biochemistry—a LANGE medical book. 1990. Twenty-second edition. Murray et al., Eds. Chapter 20: 171-178.

Mergulhão et al., Analysis of factors affecting the periplasmic production of recombinant proteins in *Escherichia coli*. J Microbiol Biotechnol. Aug. 2007;17(8):1236-41.

Mergulhão et al., Recombinant protein secretion in *Escherichia coli*. Biotechnol Adv. May 2005;23(3):177-202. Epub Jan. 8, 2005.

Meyerhof, New investigations in the kinetics of cell free alcoholic fermentation. Antonie Van Leeuwenhoek. Jan.-Apr. 1947;12(1-4):140-4.

Meynial-Salles et al., New tool for metabolic pathway engineering in *Escherichia coli*: one-step method to modulate expression of chromosomal genes. Appl Environ Microbiol. Apr. 2005;71(4):2140-4.

Michel-Reydellet et al., Amino acid stabilization for cell-free protein synthesis by modification of the *Escherichia coli* genome. Metab Eng. Jul. 2004;6(3):197-203.

Muchmore et al., Crystal structure of glutamine phosphoribosylpyrophosphate amidotransferase from *Escherichia coli*. Protein Sci. Jan. 1998;7(1):39-51.

Muktiono et al., Isolation and purification assay of ex vivo photosystem II D1 protein toward integrated biointeraction analysis. Anal Bioanal Chem. Feb. 2008;390(4):1195-202. Epub Jan. 3, 2008.

Murphy, Use of bacteriophage lambda recombination functions to promote gene replacement in *Escherichia coli*. J Bacteriol. Apr. 1998;180(8):2063-71.

Myers et al., Determination of imipenem and cilastatin in serum by high-pressure liquid chromatography. Antimicrob Agents Chemother. Jul. 1984;26(1):78-81.

Narang et al., Improved phosphotriester method for the synthesis of gene fragments. Methods Enzymol. 1979;68:90-8.

Neidhardt et al., Culture medium for enterobacteria. J Bacteriol. Sep. 1974;119(3):736-47.

Nilsen, Selective precipitation of large RNAs. Cold Spring Harb Protoc. Dec. 1, 2012;2012(12). pii: pdb.prot072322. doi: 10.1101/pdb.prot072322.

Ninh et al., Assembly and multiple gene expression of thermophilic enzymes in *Escherichia coli* for in vitro metabolic engineering. Biotechnol Bioeng. Jul. 26, 2014. doi: 10.1002/bit.25338.

Niu et al., Benzene-free synthesis of adipic acid. Biotechnol Prog. Mar.-Apr. 2002;18(2):201-11.

Noireaux et al., Principles of cell-free genetic circuit assembly. Proc Natl Acad Sci U S A. Oct. 28, 2003; 100(22):12672-7. Epub Oct. 14, 2003.

Nunez et al., The Biosynthetic Gene Cluster for the β-Lactam Carbapenem Thienamycin in Streptomyces cattleya. Chem Biol. Apr. 2003;10(4):301-11.

Ono et al., Photosynthetic electron transport and phosphorylation reactions in thylakoid membranes from the blue-green alga Anacystis nidulans. Biochim Biophys Acta. Jun. 8, 1978;502(3):477-85.

Pace et al., Photosynthetic regeneration of ATP using bacterial chromatophores. Biotechnol Bioeng. Oct. 1976;18(10):1413-23.

Park et al., Metal-catalyzed oxidation of phenylalanine-sensitive 3-deoxy-D-arabino heptulosonate-7-phosphate synthase from *Escherichia coli*: inactivation and destabilization by oxidation of active-site cysteines. J Bacteriol. Mar. 1999;181(5):1636-42.

Patnaik et al., Engineering of *Escherichia coli* central metabolism for aromatic metabolite production with near theoretical yield. Appl Environ Microbiol. Nov. 1994;60(11):3903-8.

Paul et al., Photophosphorylation in bacterial chromatophores entrapped in alginate gel: Improvement of the physical and biochemical properties of gel beads with barium as gel-inducing agent. Enzyme Microb Technol. 1980;2(4):281-87.

Peralta-Yahya et al., Microbial engineering for the production of advanced biofuels. Nature. Aug. 16, 2012;488(7411):320-8. doi: 10.1038/nature11478.

Pines et al., Expression and secretion of proteins in *E. coli*. Mol Biotechnol. Aug. 1999;12(1):25-34.

Pitera et al., Balancing a heterologous mevalonate pathway for improved isoprenoid production in *Escherichia coli*. Metab Eng. Mar. 2007;9(2):193-207. Epub Nov. 23, 2006.

Pravdic et al., Isoflurane protects cardiomyocytes and mitochondria by immediate and cytosol-independent action at reperfusion. Br J Pharmacol. May 2010;160(2):220-32. doi: 10.1111/j.1476-5381.2010.00698.x.

Qi et al., A one-step PCR-based method for rapid and efficient site-directed fragment deletion, insertion, and substitution mutagenesis. J Virolog Meth. Apr. 2008;149(1):85-90.

Ray et al., Mutational analysis of the catalytic and feedback sites of the tryptophan-sensitive 3-deoxy-D-arabino-heptulosonate-7-phosphate synthase of *Escherichia coli*. J Bacteriol. Dec. 1988;170(12):5500-6.

Reider et al., Total synthesis of thienamycin: a new approach from aspartic acid. Tetra Lett. 1982;23(22):2293-6.

Restiawaty et al., Feasibility of thermophilic adenosine triphosphate-regeneration system using Thermus thermophilus polyphosphate kinase. Process Biochemistry, Sep. 2011;46(9):1747-52.

Reyes et al., Genomic library screens for genes involved in n-butanol tolerance in *Escherichia coli*. PloS One. Mar. 8, 2011;6(3):e17678.

Rodríguez et al., Identification of transcriptional activators for thienamycin and cephamycin C biosynthetic genes within the thienamycin gene cluster from Streptomyces cattleya. Mol Microbiol. Aug. 2008;69(3):633-45.

Rodríguez et al., Transcriptional organization of ThnI-regulated thienamycin biosynthetic genes in Streptomyces cattleya. J Antibiot (Tokyo). Mar. 2010;63(3):135-8. Epub Jan. 22, 2010.

Romanowski et al., Crystal structure of the *Escherichia coli* shikimate kinase I (AroK) that confers sensitivity to mecillinam. Proteins. Jun. 1, 2002;47(4):558-62.

Sagui et al., Enzymatic synthesis of ω-carboxy-β-hydroxy-(1)-α-amino acids. Tetrahedron. May 26, 2008;64(22):5079-84.

Salis et al., Automated design of synthetic ribosome binding sites to control protein expression. Nat Biotechnol. Oct. 2009;27(10):946-50. Epub Oct. 4, 2009. Supplemental material included.

Salzmann et al., A stereocontrolled synthesis of (+)-thienamycin. J Am Chem Soc. 1980;102(19):6161-3.

Salzmann et al., A stereocontrolled, enantiomerically specific total synthesis of thienamycin. Philos Trans R Soc Lond B Biol Sci. May 16, 1980;289(1036):191-5.

Sarath et al., Use of GFP as a reporter for the analysis of sequence-specific proteases. Curr Protoc Protein Sci. Feb. 2001;Chapter 21 Unit 9 Suppl. 26: 21.9.1-.10.

Sato et al., Poly[(R)-3-hydroxybutyrate] formation in *Escherichia coli* from glucose through an enoyl-CoA hydratase-mediated pathway. J Biosci Bioeng, Jan. 2007;103(1):38-44.

Sauer et al., The soluble and membrane-bound transhydrogenases UdhA and PntAB have divergent functions in NADPH metabolism of *Escherichia coli*. J Biol Chem. Feb. 20, 2004;279(8):6613-9. Epub Dec. 3, 2003.

Schterle et al., The DsbA signal sequence directs efficient, cotranslational export of passenger proteins to the *Escherichia coli* periplasm via the signal recognition particle pathway. J Bacteriol. Oct. 2003;185(19):5706-13.

Schlehuber et al., Prediction and identification of a permissive epitope insertion site in the vesicular stomatitis virus glycoprotein. J Virol. May 2004;78(10):5079-87.

Schnell, Protein targeting to the thylakoid membrane. Annu Rev Plant Physiol Plant Mol Biol. Jun. 1998;49:97-126.

Schultheisz et al., Pathway engineered enzymatic de novo purine nucleotide synthesis. ACS Chem Biol. Aug. 15, 2008;3(8):499-511. doi: 10.1021/cb800066p.

Scopes, Glycolysis in cell-free systems. New beer in an old bottle: Eduard Buchner and the growth of biochemical knowledge. Ed A. Cornish-Bowden. 1997;151-8.

(56) References Cited

OTHER PUBLICATIONS

Scopes, Studies with a reconstituted muscle glycolytic system. The anaerobic glycolytic response to simulated tetanic contraction. Biochem J. Jan. 1974;138(1):119-23.
Sheen, Metabolic repression of transcription in higher plants. Plant Cell. Oct. 1990;2(10):1027-38.
Shi et al., Molecular properties, functions, and potential applications of NAD kinases. Acta Biochim Biophys Sin (Shanghai). May 2009;41(5):352-61.
Shiba et al., Inorganic polyphosphate and polyphosphate kinase: their novel biological functions and applications. Biochemistry (Mosc). Mar. 2000;65(3):315-23.
Shine et al., Determinant of cistron specificity in bacterial ribosomes. Nature. Mar. 6, 1975;254(5495):34-8.
Simmons et al., Translational level is a critical factor for the secretion of heterologous proteins in *Escherichia coli*. Nat Biotechnol. May 1996;14(5):629-34.
Sleeman et al., Carboxymethylproline synthase (CarB), an unusual carbon-carbon bond-forming enzyme of the crotonase superfamily involved in carbapenem biosynthesis. J Biol Chem. Feb. 20, 2004;279(8):6730-6. Epub Nov. 18, 2003.
Soares et al., Periplasmic expression of human growth hormone via plasmid vectors containing the lambdaPL promoter: use of HPLC for product quantification. Protein Eng. Dec. 2003;16(12):1131-8.
Sorci et al., Nicotinamide mononucleotide synthetase is the key enzyme for an alternative route of NAD biosynthesis in Francisella tularensis.Proc Natl Acad Sci U S A. Mar. 3, 2009;106(9):3083-8. Epub Feb. 9, 2009. Supplemental material included.
Spickler et al., Action of RNase II and polynucleotide phosphorylase against RNAs containing stem-loops of defined structure. J Bacteriol. May 2000;182(9):2422-7.
Spirin, High-throughput cell-free systems for synthesis of functionally active proteins.Trends Biotechnol. Oct. 2004;22(10):538-45. With Supplementary data.
Srinivasan et al., The Enzymatic Synthesis Of Shikimic Acid From D-Erythrose-4-Phosphate And Phosphoenolpyruvate1,2,3. J. Am. Chem. Soc. 1955;77(18):4943-4944.
Sroga et al., Periplasmic expression as a basis for whole cell kinetic screening of unnatural enzyme reactivities. Methods Enzymol. 2004;388:145-56.
Stadtman et al., Metal-catalyzed oxidation of proteins. Physiological consequences. J Biol Chem. Feb. 5, 1991;266(4):2005-8.
Stapon et al., Carbapenem biosynthesis: confirmation of stereochemical assignments and the role of CarC in the ring stereoinversion process from L-proline. J Am Chem Soc. Jul. 16, 2003;125(28):8486-93.
Stapon et al., Synthesis of (3S,5R)-carbapenam-3-carboxylic acid and its role in carbapenem biosynthesis and the stereoinversion problem. J Am Chem Soc. Dec. 24, 2003;125(51):15746-7.
Stazic et al., Antisense RNA protects mRNA from RNase E degradation by RNA-RNA duplex formation during phage infection. Nucleic Acids Res. Jun. 2011;39(11):4890-9. doi: 10.1093/nar/gkr037. Epub Feb. 15, 2011.
Stephanopoulos et al., Exploiting biological complexity for strain improvement through systems biology. Nat Biotechnol. Oct. 2004;22(10):1261-7.
Suzuki et al., Single protein production (SPP) system in *Escherichia coli*. Nat Protoc. 2007;2(7):1802-10.
Suzuki et al., Single protein production in living cells facilitated by an mRNA interferase. Mol Cell. Apr. 15, 2005;18(2):253-61.
Swartz et al., Advances in *Escherichia coli* production of therapeutic proteins. Curr Opin Biotechnol. Apr. 2001;12(2):195-201.
Swartz, Developing cell-free biology for industrial applications. J Ind Microbiol Biotechnol. Jul. 2006;33(7):476-85. Epub May 9, 2006. Review.
Swartz, Transforming biochemical engineering with cell-free biology. AIChE J. 2012;58(1):5-13.
Swartz, Universal cell-free protein synthesis. Nat Biotechnol. Aug. 2009;27(8):731-2. doi: 10.1038/nbt0809-731.

Sybesma et al., Increased production of folate by metabolic engineering of Lactococcus lactis. Appl Environ Microbiol. Jun. 2003;69(6):3069-76.
Thöny-Meyer et al., Translocation to the periplasm and signal sequence cleavage of preapocytochrome c depend on sec and lep, but not on the ccm gene products. Eur J Biochem. Jun. 15, 1997;246(3):794-9.
Tjalsma et al., Proteomics of protein secretion by Bacillus subtilis: separating the "secrets" of the secretome. Microbiol Mol Biol Rev. Jun. 2004;68(2):207-33.
Tracewell et al., Directed enzyme evolution: climbing fitness peaks one amino acid at a time. Curr Opin Chem Biol. Feb. 2009;13(1):3-9. Epub Feb. 25, 2009.
Tyo et al., Analysis of polyhydroxybutyrate flux limitations by systematic genetic and metabolic perturbations. Metab Eng. May 2010;12(3):187-95. Epub Oct. 30, 2009.
Van Bloois et al., Export of functional Streptomyces coelicolor alditol oxidase to the periplasm or cell surface of *Escherichia coli* and its application in whole-cell biocatalysis. Appl Microbiol Biotechnol. Jun. 2009;83(4):679-87. Epub Feb. 18, 2009.
Van Hees et al., Determination of low molecular weight organic acids in soil solution by HPLC. Taianta. Jan. 5, 1999;48(1):173-9.
Vander Heiden et al., Understanding the Warburg effect: the metabolic requirements of cell proliferation. Science. May 22, 2009;324(5930):1029-33. doi: 10.1126/science.1160809.
Voloshin et al., Efficient and scalable method for scaling up cell free protein synthesis in batch mode. Biotechnol Bioeng. Aug. 20, 2005;91(4):516-21.
Wahl et al., Molecular hybridization of immobilized nucleic acids: theoretical concepts and practical considerations. Methods Enzymol. 1987;152:399-407.
Wang et al., Programming cells by multiplex genome engineering and accelerated evolution. Nature. Aug. 13, 2009;460(7257):894-8. Epub Jul. 26, 2009.
Ward et al., Genomic insights into methanotrophy: the complete genome sequence of Methylococcus capsulatus (Bath). PLOS Biology. 2004;2(10):1616-28.
Weaver et al., Cloning of an aroF allele encoding a tyrosine-insensitive 3-deoxy-D-arabino-heptulosonate 7-phosphate synthase. J Bacteriol. Nov. 1990;172(11):6581-4.
Welch et al., Studies on cell-free metabolism: Ethanol production by a yeast glycolytic system reconstituted from purified enzymes. J Biotechnol. 1985;2:257-73.
Wiechert et al., A universal framework for 13C metabolic flux analysis. Metab Eng. Jul. 2001;3(3):265-83.
Wiechert, 13C metabolic flux analysis. Metab Eng. Jul. 2001;3(3):195-206.
Wilen et al., Tetrahedron report No. 38: Strategies in optical resolutions. Tetrahedron. 1977;33:2725-2736.
Williamson et al., Biosynthesis of the beta-lactam antibiotic, thienamycin, by Streptomyces cattleya. J Biol Chem. Apr. 25, 1985;260(8):4637-47.
Wilson et al., The shikimic acid pathway and polyketide biosynthesis. J Indust Microbiol Biotechnol. 1998;20:299-303.
Withers et al., Identification of isopentenol biosynthetic genes from Bacillus subtilis by a screening method based on isoprenoid precursor toxicity. Appl Environ Microbiol. Oct. 2007;73(19):6277-83. Epub Aug. 10, 2007.
Wong et al., Preparation of a mixture of nucleoside triphosphates from yeast RNA: use in enzymic synthesis requiring nucleoside triphosphate regeneration and conversion to nucleoside diphosphate sugars. J. Am. Chem. Soc. 1983;105(1):115-7.
Woodrow et al., A sequential expression system for high-throughput functional genomic analysis. Proteomics. Nov. 2007;7(21):3870-9.
Woodrow et al., Rapid expression of functional genomic libraries. J Proteome Res. Dec. 2006;5(12):3288-300.
Wuu et al., High yield cell-free production of integral membrane proteins without refolding or detergents. Biochim Biophys Acta. May 2008;1778(5):1237-50. doi: 10.1016/j.bbamem.2008.01.023. Epub Feb. 11, 2008.
Wylie et al., A single point mutation in ctp synthetase of chlamydia trachomatis confers resistance to cyclopentenyl cytosine. J Biol Chem. 1996;271:15393-400.

(56) References Cited

OTHER PUBLICATIONS

Yamaguchi et al., MqsR, a crucial regulator for quorum sensing and biofilm formation, is a GCU-specific mRNA interferase in *Escherichia coli*. J Biol Chem. Oct. 16, 2009;284(42):28746-53. Epub Aug. 18, 2009.

Yamaguchi et al., mRNA interferases, sequence-specific endoribonucleases from the toxin-antitoxin systems. Prog Mol Biol Transl Sci. 2009;85:467-500.

Yang et al., Export of methyl parathion hydrolase to the periplasm by the twin-arginine translocation pathway in *Escherichia coli*. J Agric Food Chem. Oct. 14, 2009;57(19):8901-5.

Yang et al., Rapid expression of vaccine proteins for B-cell lymphoma in a cell-free system. Biotechnol Bioeng. Mar. 5, 2005;89(5):503-11.

Ye et al., Synthetic metabolic engineering—a novel, simple technology for designing a chimeric metabolic pathway. Microb Cell Fact. Sep. 6, 2012;11:120. doi: 10.1186/1475-2859-11-120.

Yeo et al., Plasmodium falciparum CTP:phosphocholine cytidylyltransferase expressed in *Escherichia coli*: purification, characterization and lipid regulation. Biochem J. 1997;324:903-10.

Yu et al., Production of high-quality particulate methane monooxygenase in high yields from Methylococcus capsulatus (bath) with a hollow-fiber membrane bioreactor. J Bacteriol. Oct. 2003;185(20):5915-24.

Zago et al., Cloning and characterization of polyphosphate kinase and exopolyphosphatase genes from Pseudomonas aeruginosa 8830. Appl Environ Microbiol. May 1999;65(5):2065-71.

Zamboni et al., 13C-based metabolic flux analysis. Nat Protoc. 2009;4(6):878-92. Epub May 21, 2009.

Zawada et al., Effects of growth rate on cell extract performance in cell-free protein synthesis. Biotechnol Bioeng. Jul. 5, 2006;94(4):618-24.

Zawada et al., Maintaining rapid growth in moderate-density *Escherichia coli* fermentations. Biotechnol Bioeng. Feb. 20, 2005;89(4):407-15.

Zhang et al., Characterization of ChpBK, an mRNA interferase from Escherichia coli. J Biol Chem. Jul. 15, 2005;280(28):26080-8. Epub May 18, 2005.

Zhang et al., Characterization of YafO, an *Escherichia coli* toxin. J Biol Chem. Sep. 18, 2009;284(38):25522-31. Epub Jul. 17, 2009.

Zhang et al., Efficient regeneration of transgenic plants from rice protoplasts and correctly regulated expression of the foreign gene in the plants. Theor Appl Genet. 1988;76(6):835-40.

Zhang et al., Insights into the mRNA cleavage mechanism by MazF, an mRNA interferase. J Biol Chem. Feb. 4, 2005;280(5):3143-50. Epub Nov. 10, 2004.

Zhao et al., A novel high-throughput screening method for microbial transglutaminases with high specificity toward Gln141 of human growth hormone. J Biomol Screen. Feb. 2010;15(2):206-12. doi: 10.1177/1087057109356206. Epub Jan. 19, 2010.

Zhu et al., A high-energy-density sugar biobattery based on a synthetic enzymatic pathway. Nat Commun. 2014;5:3026. doi: 10.1038/ncomms4026.

PCT/US2018/055353, Apr. 23, 2020, International Preliminary Report on Patentability.

International Preliminary Report on Patentability dated Apr. 23, 2020 for Application No. PCT/US2018/055353.

Köhrer et al., Use of T7 RNA polymerase in an optimized *Escherichia coli* coupled in vitro transcription-translation system. Application in regulatory studies and expression of long transcription units. Eur J Biochem. 1996;236(1):234-239. doi:10.1111/j.1432-1033.1996.00234.x.

[No Author Listed] Retic Lysate IVTTM Kit (Par No. AM 1200) Protocol. Viewed on internet on Mar. 14, 2021 at https://assets.thermofisher.com/TFS-Assets/LSG/manuals/fm_1200.pdf. Published Nov. 3, 2008.

Nahalka et al., Nucleoside triphosphates production using recombinant *Escherichia coli* entrapped in calcium pectate gel. Biotechnology Letters vol. 24, pp. 925-930 (2002).

Saint-Girons et al., Structural and catalytic characteristics of *Escherichia coli* adenylate kinase. J Biol Chem. Jan. 15, 1987;262(2):622-9. PMID: 3027060.

U.S. Appl. No. 17/202,029, filed Mar. 15, 2021, Blake et al.

U.S. Appl. No. 17/094,718, filed Nov. 10, 2020, Cunningham et al.

* cited by examiner

CELL-FREE PRODUCTION OF RIBONUCLEIC ACID

RELATED APPLICATIONS

This application is a national stage filing under 35 U.S.C. § 371 of international application number PCT/US2016/024937, filed Mar. 30, 2016, which was published under PCT Article 21(2) in English and claims the benefit under 35 U.S.C. § 119(e) of U.S. provisional application Ser. No. 62/140,407, filed Mar. 30, 2015, each of which is incorporated by reference herein in its entirety.

BACKGROUND OF INVENTION

RNA interference (RNAi) refers to a cellular mechanism that uses the DNA sequence of a gene to turn the gene "off"—a process referred to as "silencing." In a wide variety of organisms, including animals, plants, and fungi, RNAi is triggered by double-stranded RNA (dsRNA). Double-stranded RNA (e.g., therapeutic dsRNA) has been produced in living cells and in vitro using purified, recombinant enzymes and purified nucleotide triphosphates (see, e.g., European Patent No. 1631675 A1 and U.S. Patent Application Publication No. US2014/0271559 A1). However, the large-scale production of dsRNA using such systems is challenging, inefficient, and expensive.

BRIEF SUMMARY OF INVENTION

Provided herein is a platform for cell-free production (also referred to as biosynthesis) of RNA, including dsRNA. The methods, compositions (e.g., cells and cell lysates), and systems of the present disclosure are based on a process that involves cell-free (e.g., using cell lysate(s)) degradation of polymeric RNA (e.g., mRNA, tRNA and/or rRNA) into monophosphate and diphosphate ribonucleotide monomers. Following RNA degradation, the monophosphate and diphosphate ribonucleotide monomers are converted to ribonucleotide triphosphate, and then the ribonucleotide triphosphates are polymerized to form desired RNA (e.g., dsRNA).

Thus, the present disclosure provides methods of producing a cell lysate for cell-free production of ribonucleic acid (RNA). The methods may comprise (a) culturing cells to a desired cell density, wherein the cells comprise at least one engineered nucleic acid containing a promoter operably linked to a sequence encoding a nuclease (e.g., S1 Nuclease, NucA, PNPase, RNase II, RNase III, or RNase R) that includes a protease-recognition site and is linked to a periplasmic-targeting sequence, wherein at least one endogenous ribonuclease (e.g., RNase III, RNase I, RNaseR, PNPase, RNase II, and/or RNase T) is genetically inactivated or inactivated via targeted proteolysis in the cells, (b) lysing cells produced in step (a), thereby producing a first cell lysate, and (c) incubating the first cell lysate under conditions that result in RNA depolymerization and NMP and NDP phosphorylation, thereby producing a first cell lysate containing nucleotide 5'-monophosphates (or a mixture of nucleotide 5'-monophosphates and nucleotide 5'-diphosphates).

In some embodiments, the methods further comprise (d) culturing cells that comprise (i) at least one engineered nucleic acid containing a promoter operably linked to a sequence encoding a cognate protease that cleaves the protease-recognition site of the nuclease or targeted endogenous RNases, wherein the cognate protease (e.g., human rhinovirus 3C protease) is linked to a periplasmic-targeting sequence, (ii) at least one engineered nucleic acid containing a promoter operably linked to a sequence encoding a nucleotide kinase (e.g., uridylate kinase, cytidylate kinase, guanylate kinase, adenylate kinase, nucleoside phosphate kinase, pyruvate kinase, and polyphosphate kinase), (iii) at least one engineered nucleic acid containing a promoter operably linked to a sequence encoding an RNA polymerase, and (iv) an engineered deoxyribonucleic acid (DNA) template containing a promoter operably linked to a sequence encoding a RNA transcript, wherein at least one endogenous ribonuclease is genetically inactivated or inactivated via targeted proteolysis in the cells; and (e) lysing cultured cells produced in step (d), to produce a second cell lysate.

In some embodiments, the methods further comprise combining the first cell lysate produced in step (b), the second cell lysate produced in step (e), and polyphosphate and/or glucose, thereby producing a mixture; and incubating the mixture under conditions that result in the production of RNA (e.g., dsRNA).

In some embodiments, the methods comprise (a) culturing cells to a desired cell density, wherein the cells comprise (i) at least one engineered nucleic acid containing a promoter operably linked to a sequence encoding a nuclease that includes a protease-recognition site and is linked to a periplasmic-targeting sequence, and (ii) at least one engineered nucleic acid containing a promoter operably linked to a sequence encoding a nucleotide kinase, wherein at least one endogenous ribonuclease is genetically inactivated or inactivated via targeted proteolysis in the cells, (b) lysing cells produced in step (a), thereby producing a first cell lysate, and (c) incubating the first cell lysate with polyphosphate and/or glucose under conditions that result in RNA depolymerization, thereby producing a first cell lysate containing a mixture of nucleotide 5'-triphosphates.

In some embodiments, the methods further comprise (d) culturing cells that comprise (i) at least one engineered nucleic acid containing a promoter operably linked to a sequence encoding a cognate protease that cleaves the protease-recognition sequence of the nuclease, wherein the cognate protease is linked to a periplasmic-targeting sequence, (ii) at least one engineered nucleic acid containing a promoter operably linked to a sequence encoding an RNA polymerase, and (iii) an engineered deoxyribonucleic acid (DNA) template containing a promoter operably linked to a sequence encoding a RNA transcript that includes complementary domains linked by a hinged domain, wherein at least one endogenous ribonuclease is genetically inactivated or inactivated via targeted proteolysis in the cells, and (e) lysing cultured cells produced in step (d), to produce a second cell lysate.

In some embodiments, the methods further comprise combining the first cell lysate produced in step (b), the second cell lysate produced in step (e), and polyphosphate and/or glucose, thereby producing a mixture; and incubating the mixture under conditions that result in production of RNA.

Also provided herein are engineered cells and cell lysates comprising a nuclease that includes a protease-recognition site and is linked to a periplasmic-targeting sequence, a nucleotide kinase, and a mixture of nucleotide 5'-monophosphates and nucleotide 5'-diphosphates.

Further provided herein are engineered cells and cell lysates comprising an RNA polymerase, and an engineered DNA template encoding an RNA.

Some aspects of the present disclosure provide cell-free methods of producing ribonucleic acid (RNA), the methods comprising (a) combining a first cell lysate with a second cell lysate, wherein the first cell lysate comprises (i) a nuclease that includes a protease-recognition site, and (ii) nucleotide 5'-monophosphates, and the second cell lysate comprises (iii) a cognate protease that cleaves the protease-recognition site of the nuclease, (iv) nucleotide kinase, (v) an RNA polymerase, and (vi) an engineered deoxyribonucleic acid (DNA) template containing a promoter operably linked to a sequence encoding an RNA of interest, thereby forming a reaction mixture, and (b) incubating the reaction mixture under conditions that result in production of the RNA of interest (e.g., a double-stranded RNA of interest).

In some embodiments, the methods comprise (a) combining a first cell lysate with a second cell lysate, wherein the first cell lysate comprises (i) a nuclease that includes a protease-recognition site and is linked to a periplasmic-targeting sequence, (ii) nucleotide kinase and polyphosphate and/or glucose, and (iii) nucleotide 5'-triphosphates, and the second cell lysate comprises (iv) a cognate protease that cleaves the protease-recognition site of the nuclease, (v) an RNA polymerase, and (vi) an engineered deoxyribonucleic acid (DNA) template containing a promoter operably linked to a sequence encoding an RNA of interest, thereby forming a reaction mixture, and (b) incubating the reaction mixture under conditions that result in production of the RNA of interest (e.g., a double-stranded RNA of interest).

In any one of the embodiments provided herein, a cell lysate or reaction mixture may be free of nuclease activity.

The details of several embodiments of the invention are set forth in the accompanying Figures and the Detailed Description. Other features, objects, and advantages of the invention will be apparent from the description and from the claims.

DETAILED DESCRIPTION OF INVENTION

Figure 1:
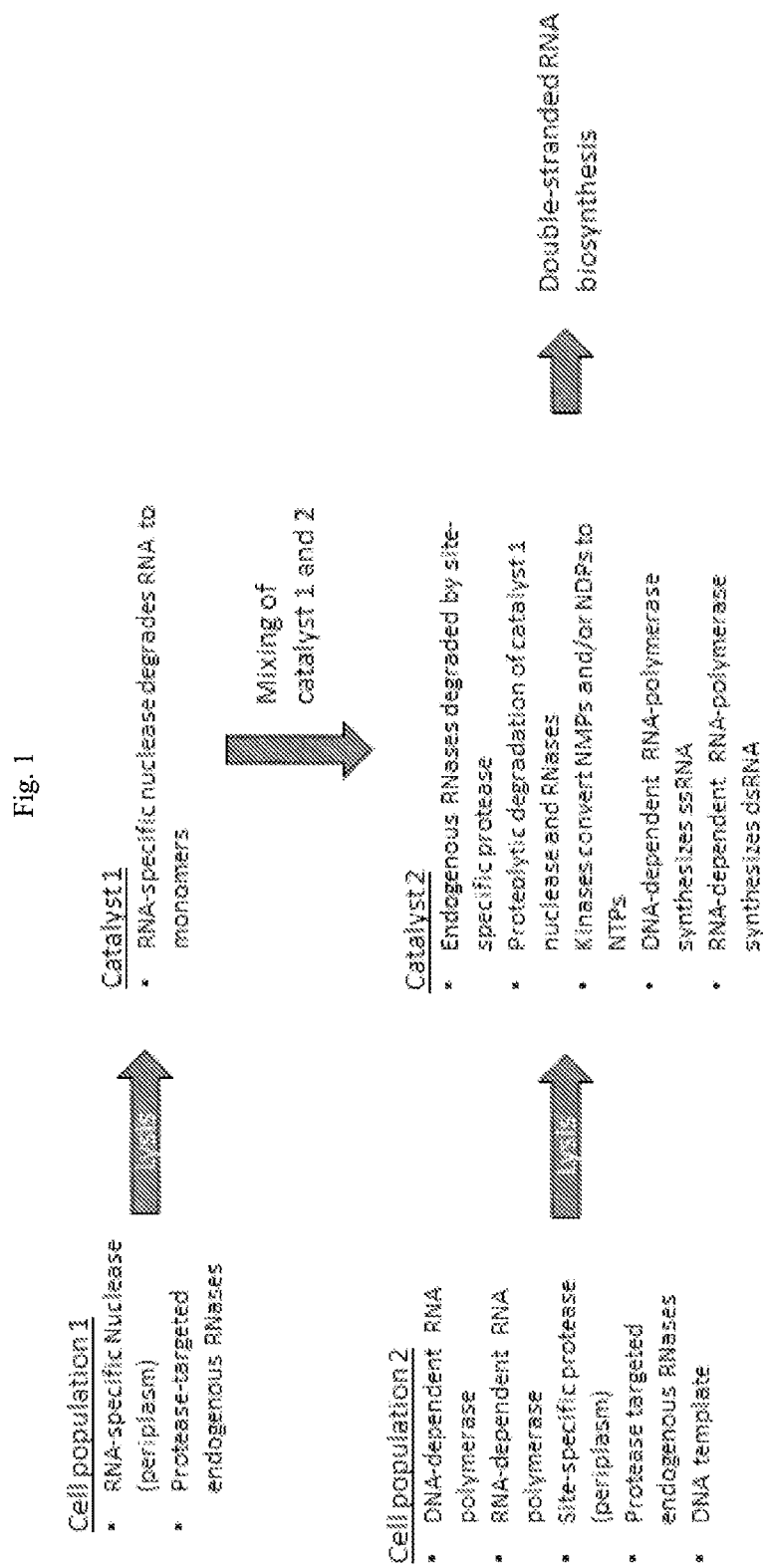
FIG. 1 shows a flowchart of an example of a process for double-stranded ribonucleic acid (dsRNA) biosynthesis. In this example, cells of one population express an engineered RNA-specific nuclease, sequestered in the periplasm, and at least one engineered protease-targeted endogenous RNase. Cells of another population express an engineered DNA-dependent RNA polymerase and/or RNA-dependent RNA polymerase, an engineered site-specific protease sequestered to the periplasm, at least one protease-targeted endogenous RNase, and an engineered DNA template encoding a desired RNA.

Provided herein, in some aspects, are methods, compositions, and systems for the cell-free production of ribonucleic acid (RNA), such as double-stranded RNA (dsRNA). The methods provided herein, conceptually, involve three main processes: (1) the degradation of intracellular polymeric RNA into nucleotide monomers—a combination of nucleotide monophosphates (NMPs) and nucleotide diphosphates (NDPs), (2) the conversion of the NMPs and NDPs to nucleotide triphosphates (NTPs), which serve as "building blocks" for the formation of polymeric RNA, and (3) the polymerization of the NTPs to produce RNA, including dsRNA. In some embodiments, cells of one population are engineered to produce the products necessary for steps 1 and 2 of the process, while cells of another population are engineered to produce products (e.g., enzymes and nucleic acid template) necessary for step 3 of the process. Cell lysates produced from each cell population are then combined for the cell-free production of RNA. In other embodiments, cells of one population are engineered to produce the products necessary for step 1 of the process, while cells of another population are engineered to produce products (e.g., enzymes and nucleic acid template) necessary for steps 2 and 3 of the process. Cell lysates produced from each cell population are then combined for the cell-free production of RNA.

It should be understood that while the RNA production process described herein is described conceptually in "steps," the steps of the process do not need to be performed separately (e.g., in a separate cell lysate or separate reaction mixture). For example, the products necessary for step 1 of the process may be expressed by one cell population, the products necessary for step 2 of the process may be expressed by another cell population, and the products necessary for step 3 of the process may be expressed by yet another cell population. Alternatively, the products necessary for steps 1 and 2 of the process may be expressed by one cell population, and the products necessary for step 3 of the process may be expressed by another cell population. Further, the products necessary for step 1 of the process may be expressed by one cell population, and the products necessary for steps 2 and 3 of the process may be expressed by another cell population.

It should also be understood that steps 1, 2, and 3 need not be performed sequentially. For example, a population of cells expressing products for one, or more than one, step may be cultured in parallel with a different population of cells expressing products for one, or more than one, step of the cell-free RNA production process of the present disclosure.

Step 1: Cell-Free Production of Nucleotide 5'-Monophosphates (5'-NMPs) and/or Nucleotide 5'-Diphosphates (5'-NDPs)

Some aspects of the present disclosure provide methods and compositions for the degradation of intracellular polymeric RNA into nucleotide monomers—a combination of nucleotide monophosphates (NMPs) and nucleotide diphosphates (NDPs). *Escherichia coli* (*E. coli*) cells can contain up to 25% RNA by weight. This RNA exists almost entirely in an oligomeric state in one of three forms: tRNA, rRNA, and mRNA. This RNA can be depolymerized to produce monomeric ribonucleotides that can serve as the building blocks for RNA biosynthesis.

Chemical means of depolymerization lead to the production of a mixture of 3'-NMPs and 5'-NMPs. 3'-NMPs cannot be used for dsRNA synthesis, and, therefore, chemical depolymerization decreases overall yield of the final RNA product. An alternative to chemical depolymerization of RNA is enzymatic depolymerization using nucleases, as described herein. Non-limiting examples of nucleases that may be used in accordance with the present disclosure are listed in Table 1.

TABLE 1

Example nucleases for RNA depolymerization to 5'-NMPs and 5'-NDPs

| Nuclease | Host Organism(s) | EC # |
|---|---|---|
| S1 Nuclease | *Vigna radiate, Aspergillus oryzae, Apium graveolens*, others | 3.1.30.1 |
| NucA | *Serratia marcescens* | 3.1.30.2 |
| PNPase | *E. coli* | 2.7.7.8 |
| RNase II | *E. coli* | 3.1.13.1 |
| RNase III | *E. coli* | 3.1.26.3 |
| RNase R | *E. coli* | 3.1.13.— |

Existing processes for the enzymatic depolymerization of RNA to 5'-NMPs (as described in, e.g., EP1587947B1, U.S. Pat. Nos. 3,223,592, and 2,844,514, each of which is incorporated herein by reference) typically involve mixing exogenous nucleases and lysed *Saccharomyces cerevisiae* cells and incubating the mixture to produce monomeric NMPs. These NMPs are typically the end product and are used, for example, as flavoring additives in food products.

The present disclosure, by contrast, encompasses enzymatic depolymerization whereby an engineered cell (e.g., an engineered *E. coli* cell) expresses, for example, one or more nucleases (e.g., see Table 1) in the periplasm of the cell. Periplasmic nuclease expression ensures that cytotoxic RNA depolymerization does not occur during cell growth. Upon cell lysis, the periplasmically-expressed nuclease(s) is/are released from the periplasm and contact cellular polymeric RNA (e.g., an RNA containing two or more contiguous ribonucleotides), thereby depolymerizing the polymeric RNA into 5'-NMPs and/or 5'-NDPs. The resulting 5'-NMPs and/or 5'-NDPs, referred to herein as "monomers," are used as starting materials for the polymerization of a particular RNA of interest (referred to as an RNA product), such as, for example, a dsRNA, without (or without significant) purification or separation of lysate components. It should be understood, however, that following the production of RNA, as provided herein, the RNA may be purified for use as a therapeutic agent.

The present disclosure, in some embodiments, contemplates the direct use of the 5'-NMP and/or 5'-NDP monomers in RNA polymerization. However, the presence of active nucleases, under some conditions, may result in depolymerization of a desired dsRNA product. Thus, provided herein is a means to functionally inactivate cellular nuclease(s) (e.g., an overexpressed nuclease), to permit use of the monomers as substrates in subsequent RNA polymerization reactions without the need for purification of the monomers. Functional inactivation of a nuclease following RNA depolymerization may be achieved, in some embodiments, by targeted proteolysis, as described, for example, U.S. Publication No. 2012/0052547 A1, published on Mar. 1, 2012; and International Publication No. WO 2015/021058 A2, published Feb. 12, 2015, each of which is incorporated herein by reference). Other means of targeted/inducible protein inactivation are also contemplated herein.

Step 2: Cell-Free Conversion of 5'-NMPs and 5'-NDPs to 5'-NTPs

Some aspects of the present disclosure provide methods and compositions for the conversion of the NMPs and NDPs to nucleotide triphosphates (NTPs), which serve as "building blocks" for the formation of polymeric RNA. Processes involving purified proteins or cell extracts for converting 5'-NMPs and 5'-NDPs to 5'-NTPs are known (e.g., U.S. Pat. No. 6,022,713, incorporated herein by reference). Non-limiting examples of NMP kinases that may be used to convert 5'-NMPs to 5'-NDPs in accordance with the present disclosure are listed in Table 2. As would be appreciated by one of skill in the art, any enzyme or other agent with the desired kinase activity may be used in the present invention. In some embodiments, adenosine triphosphate (ATP) or guanosine triphosphate (GTP) is the phosphate donor.

TABLE 2

Example NMP kinases

| Enzyme Name | Host Organism | EC # | Reaction |
|---|---|---|---|
| Uridylate kinase | *E. coli* | 2.7.4.22 | UMP + ATP → UDP + ADP |
| Cytidylate kinase | *E. coli* | 2.7.4.25 | CMP + ATP → CDP + ADP |
| Guanylate kinase | *E. coli* | 2.7.4.8 | GMP + ATP → GDP + ADP |
| Adenylate kinase | *E. coli* | 2.7.4.3 | AMP + ATP → 2 ADP |

Figure 2:
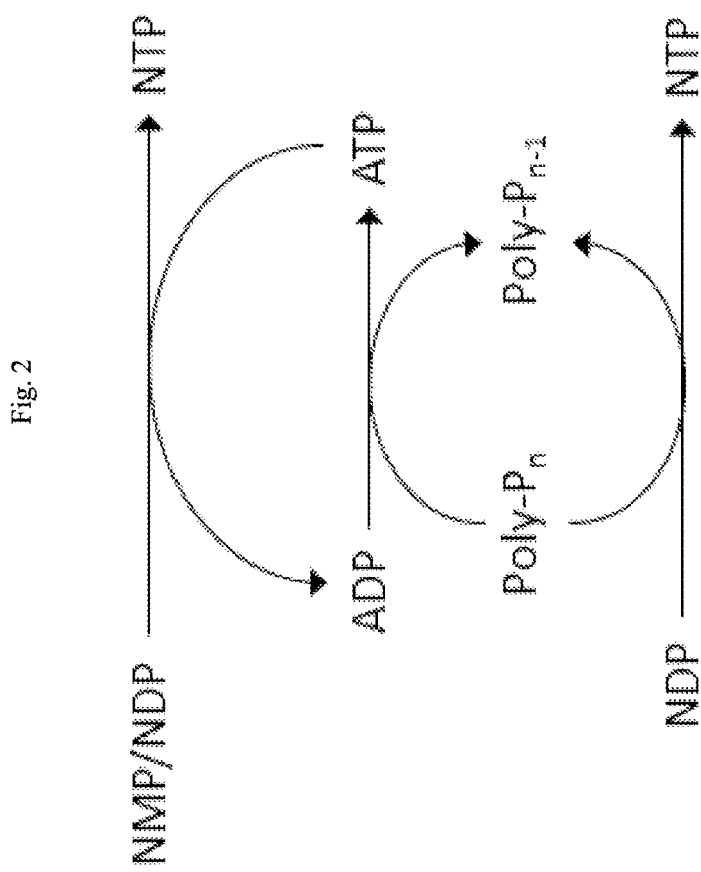
FIG. 2 shows a schematic of polyphosphate-catalyzed conversion of nucleotide monophosphate/diphosphate (NMP/NDP) to nucleotide triphosphate (NTP).

Non-limiting examples of NDP kinases that may be used to convert NDPs to NTPs in accordance with the present disclosure are listed in Table 3. The phosphate donor for nucleoside diphosphate kinase (Ndk) is ATP or GTP, the phosphate donor for pyruvate kinase (Pyk) is phosphoenolpyruvate (PEP), and the phosphate donor for polyphosphate kinase (Ppk) is polyphosphate. See FIG. 2 for an illustration of a polyphosphate-catalyzed process of the present disclosure. As would be appreciated by one of skill in the art, any enzyme or other agent with the desired kinase activity may be used in accordance with the present invention.

TABLE 3

Example NDP kinases

| Enzyme Name | Host Organism | EC # | Reaction |
|---|---|---|---|
| Nucleoside phosphate kinase | *E. coli* | 2.7.4.6 | NDP + ATP → NTP + ADP |
| Pyruvate kinase | *E. coli* | 2.7.1.40 | NDP + PEP → NTP + pyruvate |
| Polyphosphate kinase | *E. coli* | 2.7.4.1 | NDP + polyphosphate$_n$ → NTP + polyphosphate$_{n-1}$ |

Cell lysates of the present disclosure are used for cell-free enzymatic conversion of (1) NMPs to NDPs, (2) NDPs to NTPs, and (3) NTPs to dsRNA. In some embodiments, it is advantageous to eliminate/delete or inactivate in cell lysate(s) enzymes that degrade NMPs, NDPs, and/or NTPs. Non-limiting examples of enzymes that may be deleted or inactivated in accordance with the present disclosure are listed in Table 4. Thus, in some embodiments, the present disclosure contemplates engineering cells that do not express, or that express an inactive or inactivatable form of, at least one (e.g., 1, 2, 3, or 4) of the enzymes listed in Table 4.

TABLE 4

Examples of enzymes that degrade NMPs, NDPs, and NTPs

| Enzyme Name | Host Organism | EC # | Reaction |
|---|---|---|---|
| Nucleoside monophosphatase (aka 5'-nucleotidase) | *E. coli* | 3.1.3.5 | NMP + H$_2$O → nucleoside + P$_i$ |
| Nucleoside diphosphatase | *E. coli* | 3.6.1.6 | NDP + H$_2$O → NMP + P$_i$ + H$^+$ |
| Nucleoside triphosphatase | *E. coli* | 3.6.1.15 | NTP + H$_2$O → NDP + P$_i$ + H$^+$ |

TABLE 4-continued

Examples of enzymes that degrade NMPs, NDPs, and NTPs

| Enzyme Name | Host Organism | EC # | Reaction |
|---|---|---|---|
| Nucleoside triphosphate phosphohyrolase | E. coli | 3.6.1.19 | NTP + H$_2$O → NMP + PP$_i$ + H$^+$ |

Enzymatic conversion of (1) NMPs to NDPs, (2) NDPs to NTPs, and (3) NTPs to dsRNA requires, in some instances, a high-energy phosphate donor feedstock (e.g., polyphosphate). In some embodiments, it is advantageous to eliminate/delete or inactivate in cell lysate(s) enzymes that degrade polyphosphate. A non-limiting example of such an enzyme is E. coli exopolyphosphatase (EC 3.6.1.1; polyphosphate$_n$+H$_2$O→polyphosphate$_{n-1}$+P$_i$). Thus, in some embodiments, the present disclosure contemplates engineering cells that do not express, or that express an inactive or inactivatable form of, exopolyphosphatase. The present disclosure also contemplates the inactivation of other phosphatase enzymes, for example, through protease targeting.

In some embodiments, the activity of an enzyme (e.g., a nuclease) is eliminated from a cell by deletion of the cognate gene from the genome of the host (referred to as a gene "knockout"), provided the activity is non-essential for cell viability. In some embodiments, the activity of an enzyme is inhibited or reduced in a controllable manner using, for example, targeted proteolysis, as described, for example, U.S. Publication No. 2012/0052547 A1, published on Mar. 1, 2012; and International Publication No. WO 2015/021058 A2, published Feb. 12, 2015, each of which is incorporated herein by reference). Other means of targeted enzyme inactivation are also contemplated herein.

Step 3: Cell-Free Production of Ribonucleic Acid (RNA) and/or Double-Stranded RNA (dsRNA)

Some aspects of the present disclosure provide methods and compositions for the polymerization of NTPs to produce RNA, including dsRNA. Enzymatically-derived 5'-NTPs are polymerized into RNA using an RNA polymerase that produces an RNA transcript. Non-limiting examples of RNA polymerases that may be used in accordance with the present disclosure are listed in Table 5.

TABLE 5

Examples of polymerases for the conversion of NTPs to RNA

| Enzyme Name | Host Organism | Function |
|---|---|---|
| T7 RNA Polymerase | T7 Phage | DNA-dependent RNA polymerase |
| Φ6 RdRP | Phage Φ6 | RNA-dependent RNA polymerase |

Production of dsRNA Using a DNA-Dependent RNA Polymerase.

Some aspects of the present disclosure are directed to the cell-free production of double-stranded RNA (dsRNA). In some embodiments, a dsRNA molecule is encoded by a DNA template that contains a promoter operably linked to a sequence encoding RNA (e.g., an RNA transcript). In some embodiments, the RNA contains two complementary domains linked via a hinge domain. With reference to the example shown in FIG. 3, upon binding of complementary domains (domain 1 and domain 3) of single-stranded RNA (ssRNA) template to each other, the hinge domain (domain 2) forms a loop-like structure.

Two nucleic acid domains (e.g., discrete nucleotide sequences) are "complementary" to one another if they base-pair, or bind, to each other to form a double-stranded nucleic acid molecule via Watson-Crick interactions (also referred to as hybridization). As used herein, "binding" refers to an association between at least two molecules or two regions of the same molecule due to, for example, electrostatic, hydrophobic, ionic, and/or hydrogen-bond interactions under physiological conditions. In some embodiments, a complementary domain has a length of 4 to 1000 nucleotides, or more. For example, a complementary domain may have a length of 4 to 10, 4 to 20, 4 to 30, 4 to 50, 4 to 60, 4 to 70, 4 to 80, 4 to 90, 4 to 100, 4 to 200, 4 to 300, 4 to 400, or 4 to 500, or 4 to 1000 nucleotides. In some embodiments, a complementary domain has a length of 15, 16, 17, 18, 19, 20, 21, 22, 23, 24, or 25 nucleotides. In some embodiments, a complementary domain has a length of 4, 5, 6, 7, 8, 9, 10, 15, 20, 25, 30, 35, 40, 45, 50, 55, 60, 65, 70, 75, 80, 85, 90, 95 or 100 nucleotides.

In some embodiments, one of the two complementary domains is target-specific, referred to here as the (+) complementary domain. That is, a complementary domain may be designed to be complementary (e.g., identical) to a target nucleic acid of interest. Thus, in some embodiments, a (+) complementary domain is designed to be complementary to a target nucleic acid, and a (−) complementary domain is designed to be complementary to the (+) complementary domain.

A "hinge domain" in the context of the nucleic acids of the present disclosure refers to the single-stranded region that separates and is between "complementary domains." Typically, a hinge domain is non-specific, meaning that it is not designed to bind to another nucleic acid, such as a target nucleic acid. A hinge domain forms a loop-like structure upon binding of the complementary domains to form a double-stranded region. In some embodiments, a hinge domain has a length of 4 to 500 nucleotides, or more. For example, a hinge domain may have a length of 4 to 10, 4 to 20, 4 to 30, 4 to 50, 4 to 60, 4 to 70, 4 to 80, 4 to 90, 4 to 100, 4 to 200, 4 to 300, 4 to 400, or 4 to 500 nucleotides. In some embodiments, a hinge domain has a length of 4, 5, 6, 7, 8, 9, 10, 15, 20, 25, 30, 35, 40, 45, 50, 55, 60, 65, 70, 75, 80, 85, 90, 95 or 100 nucleotides.

Figure 3:
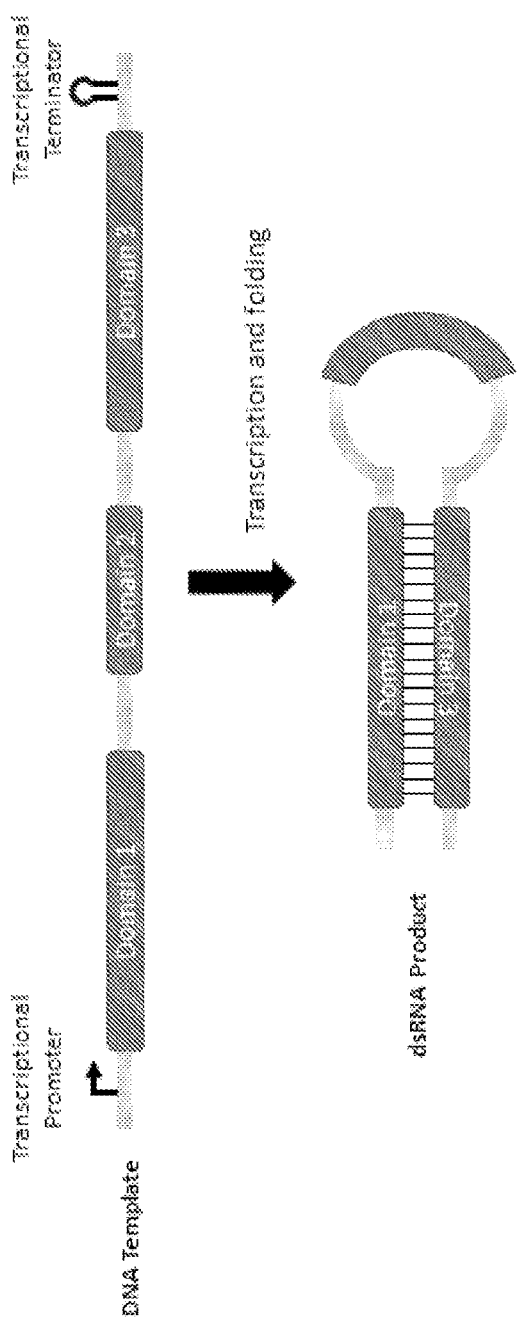
FIG. 3 shows a schematic of the conversion of an engineered DNA template to a dsRNA product.
Figure 4:
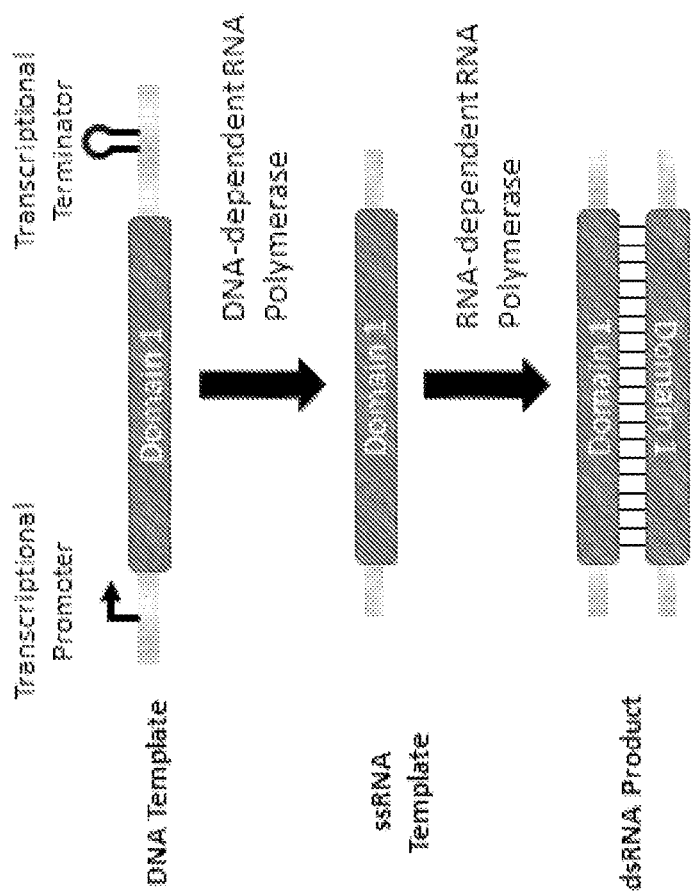
FIG. 4 shows a schematic of the conversion of an engineered DNA template to a dsRNA product via an intermediate single-stranded RNA (ssRNA).

It should be understood that a "double-stranded RNA" of the present disclosure encompasses wholly double-stranded molecules, which do not contain a single-stranded region (e.g., a loop or overhang), as well as partially double-stranded molecules, which contain a double-stranded region and a single-stranded region (e.g., a loop or overhang). The dsRNA product depicted at the bottom of FIG. 3 is considered a partially double-stranded molecule, while the dsRNA product depicted at the bottom of FIG. 4 is considered a wholly double-stranded molecule.

Cell-free production of an RNA, including dsRNA, may be catalyzed, in some embodiments, by a highly processive DNA-dependent T7 RNA polymerase encoded from the T1 gene, although other DNA-dependent RNA polymerases may be used in accordance with the present disclosure. Thus, in some embodiments, an engineered DNA template includes a T7-specific promoter operably linked to a nucleotide sequence encoding an RNA molecule of interest. Typically, a promoter is located immediately 5' of the coding sequence. In some embodiments, engineered DNA template includes a T7-specific transcriptional terminator. A transcriptional terminator is typically located immediately 3' of the coding sequence. As shown in FIG. 3, sequence encoding domain 1, domain 2, and domain 3 is flanked at each end by a transcription promoter and a transcriptional terminator. Similarly, as shown in FIG. 4, sequence encoding domain 1 is flanked at each end by a transcription promoter and a transcriptional terminator.

In some embodiments, a DNA template (e.g., containing a 5' promoter and a 3' terminator) is located on an expression vector containing an endonuclease restriction site outside of the coding region. In such embodiments, a cell may be engineered to express a cognate restriction endonuclease that cleaves the endonuclease restrictions site of the vector, resulting in linearization of the DNA template. Linearization permits, for example, "run-off transcription" of the desired RNA molecule, improving overall yield. In some embodiments, the cognate restriction endonuclease is I-SceI. Other restriction endonucleases are known and may be used in accordance with the present disclosure. Non-limiting examples include EcoRI, EcoRII, BamHI, HindIII, TaqI, NotI, HinFI, Sau3AI, PvuII, SmaI, HaeIII, HgaI, AluI, EcoRV, EcoP15I, KpnI, PstI, SacI, SalI, ScaI, SpeI, SphI, StuI, and XbaI, FokI, AscI, AsiAI, NotI, FseI, PacI, SdaI, SgfL, SfiI, PmeI.

Production of dsRNA Using an RNA-Dependent RNA Polymerase.

In some embodiments, a dsRNA molecule is encoded by a DNA template that contains a promoter operably linked to a sequence encoding a messenger RNA (mRNA) that contains a single target domain (e.g., a domain that is complementary to a target nucleic acid of interest). With reference to the example shown in FIG. 4, following production of a single-stranded RNA (ssRNA), an RNA-dependent RNA polymerase (RdRP) may be used to synthesize a dsRNA of interest. In some embodiments, an RdRP isolated from phage Φ6 is used to synthesize dsRNA. Phage Φ6 is a double stranded RNA virus that infects members of the genus *Pseudomonas*. Phage Φ6 is one of the most well-studied dsRNA viruses. This phage encodes an RdRP that is capable of synthesizing RNA using an RNA template, yielding a dsRNA molecule. The Φ6 RdRP is capable of polymerizing RNA absent a primer molecule, thus the polymerase requires only template RNA (Wright, S. et al, 2012. *Journal of Virology*. March; 86(5):2837-49; Van Dijk, A A., et al, 2004. *J Gen Virol. May;* 85(Pt 5), incorporated herein by reference). Other viral RdRPs are contemplated herein.

In some embodiments, the DNA template encoding the RNA containing a single target domain is transcribed using a DNA-dependent RNA polymerase, such as, for example, the T7 RNA polymerase, and then the resulting RNA transcript serves as a template for an RNA-dependent RNA polymerase, such as, for example, the phage Φ6 RdRP, to synthesize a complementary RNA molecule, yielding a dsRNA (e.g., FIG. 4).

Inhibition of Host RNA Polymerase

Lysis and depolymerization of cellular ribonucleic acids as described above typically yields a pool of 5'-ribonucleotides. Competition between the native RNA polymerase and the heterologous T7 RNA polymerase and/or Φ6 RdRP for these pools of ribonucleotides may, in some instances, decrease yield of the desired RNA product. Nonetheless, RNA polymerase is essential for the viability of intact cells. Thus, provided herein are at least two methods for disrupting native RNA polymerase function. For example, targeted proteolysis, as described elsewhere herein, may be used to disrupt activity of at least one of the key components of the native RNA polymerase, leading to sufficient disruption of RNA polymerase activity. As another example of disrupting native RNA polymerase function, the T7 phage protein Gp2 may be expressed. Gp2 is the second T7 phage protein that is translated following infection of *E. coli* by T7 phage. This protein disrupts host RNA polymerase function thus eliminating competition between native RNA polymerase and the phage polymerase (Bae, B. et al, 2013. *Proc Natl Acad Sci USA*. December 3; 110(49):19772-7).

Improved Product Yields Through Inactivation of Host Ribonucleases

One aspect to the cell-free production of RNA (e.g., dsRNA) is the inhibition/prevention of product degradation during and after synthesis. In all living organisms, the ability to cleave and process RNA molecules is essential to viability. Numerous native *E. coli* enzymes, referred to as ribonucleases, or RNases, catalyze the depolymerization of RNA molecules with varying affinities. Some of these RNases, including RNase D, responsible for tRNA maturation, are highly substrate specific, while others, including RNase I, are capable of depolymerizing a wide range of RNA polymers. Non-limiting examples of RNases, as well as their cognate genes, proposed activities, and example sequences are shown in Table 6.

In some embodiments, cell are engineered such that 50% to 100% (e.g., 50%, 55%, 60%, 65%, 70%, 75%, 80%, 85%, 90%, 95%, 96%, 97%, 98%, 99%) of endogenous ribonuclease (RNase) activity that would depolymerize or otherwise degrade the RNA product of interest is inactivated or deleted in cell lysate(s) produced from the engineered cells. This may be achieved by any means known in the art. In some embodiments, this is achieved by a chromosomal deletion of an endogenous gene encoding an RNase, provided the RNase is not essential for cell viability. Examples of genes that may be deleted from the genome of cells are listed in Table 6. In some embodiments, if the RNase is essential for cell viability, the cells may be engineered to contain endogenous RNases engineered to be sensitive to targeted proteolytic degradation (e.g., expressed from their native/endogenous promoters). Examples of RNases/nucleases that may be protease-targeted, as provided herein, are listed in Table 7. In some embodiments, a combination of the foregoing approaches is used. Alternatively, or in addition, nuclease inhibitors may be used (e.g., added to a cell lysate or reaction mixture). It should be noted that simultaneous deletion of pnp and rnb is lethal to a cell. Thus, the present disclosure also contemplates protease-targeting of one or both of the encoded enzymes.

TABLE 6

Examples of activities whose disruption could result in improved dsRNA yields in the dsRNA production strain

| Enzyme | Gene | Function |
| --- | --- | --- |
| RNase III | rnc | Cleaves dsRNA, rRNA and some mRNA |
| RNase I | rna | General ribonuclease, broad substrate specificity. Localizes to periplasm. |
| RNaseR | rnr | Cleaves some dsRNA, poly-A mRNA, mRNA and rRNA |
| PNPase | pnp | General mRNA degradation, tRNA maturation and degradation. |
| RNase II | rnb | Exonuclease. Plays a role in tRNA processing |
| RNase T | rnt | Processing of tRNAs, rRNA and other stable RNAs. Capable of degrading ssDNA and ssRNA. |

TABLE 7

Examples of ribonucleases that could be inactivated
via targeted proteolytic degradation

| Enzyme | Gene | Function |
| --- | --- | --- |
| RNase R | rnr | Cleaves some dsRNA, poly-A mRNA, mRNA and rRNA |
| RNase E | rne | Processes rRNA, tRNA and other RNAs. Associates with the "degradasome" |
| PNPase | pnp | General mRNA degradation, tRNA maturation and degradation. |
| RNase II | rnb | Exonuclease. Plays a role in tRNA processing |

The *E. coli* RNase III enzyme preferentially cleaves dsRNA as well as some single-stranded mRNA molecules (Robertson, H D and J. J. Dunn. 1974. *J Biol Chem*. April 25; 250(8):3050-6.; Lybecker, M. et al. 2014. The double-stranded transcriptome of *Escherichia coli*. *Proc Natl Acad Sci USA*. February 25; 111(8):3134-9, each of which is incorporated herein by reference). The presence of this enzyme in a cell-free system may limit the ability to accumulate high concentrations of dsRNA, as the product would readily be cleaved. The gene encoding RNase III, rnc, is not essential for cell viability, thus the present disclosure, in some embodiments, contemplates the chromosomal deletion/mutation of rnc in engineered cells, prior to cell-free production of an RNA of interest, or protease-targeting of RNase III (Takiff, H. E. et al. 1989. *J Bacteriol*. May; 171(5):2581-90, each of which is incorporated herein by reference).

Similarly, the broad substrate exoribonuclease RNase I is not essential for the viability of *E. coli*. RNase I, which localizes to the periplasmic space in intact *E. coli* cells, catalyzes the depolymerization of a wide range of RNA molecules including rRNA, mRNA and tRNA (Neu, H. C. and L. A. Heppel. 1964. *J Biol Chem*. November; 239:3893-900). Under physiological conditions the periplasmic localization of this enzyme means that the enzyme has little impact on RNA stability within the cell. However, the mixing of periplasm and cytoplasm in the cell-free methods of the present disclosure permits RNase I access to cellular RNA. Its presence may significantly reduce product output through the degradation of the ssRNA intermediate. Thus, the present disclosure, in some embodiments, contemplates the chromosomal deletion/mutation of rna, the gene encoding RNase I, or the protease-targeting of RNase I (Kaplan, R. and D. Apirion. 1974. *J Biol Chem*. January 10; 249(1):149-51, incorporated herein by reference).

Two other broad-substrate exoribonucleases, RNase R and RNase T, catalyze the depolymerization of dsRNA, rRNA, tRNA, and mRNA as well as small unstructured RNA molecules (Cheng and Deutscher. 2002; Cheng and Deutscher. 2005; Vincent and Deutscher. 2009; Viswanathan et al., 1998). The genes that encode RNase R and RNase T, rnr and rnt, respectively, are not essential for cell viability. Thus, the present disclosure, in some embodiments, contemplates the chromosomal deletion/mutation of rnr and/or rnt, or the protease-targeting of RNase R and/or RNase.

A central component for RNA turnover within living *E. coli* cells, specifically mRNA, is a group of enzymes referred to as the degradasome (Bandyra, K. and B. F. Luisi, 2013. *RNA Biol*. April; 10(4):627-35; A. J. Carpousis, 2002. *Biochem Soc Trans*. April; 30(2):150-5, each of which is incorporated herein by reference). This degradasome contains of two ribonucleases, RNase E and PNPase, a RNA helicase, and several other proteins with roles in RNA degradation. RNase E functions as an endoribonuclease that regulates rRNA maturation as well as mRNA turnover. RNase E, without being bound by theory, may work in concert with exoribonucleases, such as PNPase and RNase II, to constantly turn over cellular mRNA pools. In this model, RNase E first cleaves the target RNA molecule internally, and the smaller RNA fragments are subsequently depolymerized to monomers. Disruption of the gene encoding RNase E, rne, is lethal in *E. coli* (Goldblum, K. and D. Apririon, 1981. *J Bacteriol*. April; 146(1):128-32, incorporated herein by reference). Thus, the present disclosure, in some embodiments, contemplates the protease-targeting of RNase R and/or RNase. In some embodiments, the present disclosure contemplates protease-targeting of only one of PNPase and RNase II.

As described above, *E. coli* PNPases, encoded by the pnp gene associates with the degradasome wherein it serves as an exoribonuclease with 3'→5' processivity (A. J. Carpousis, 2002). PNPase plays a role in mRNA degradation as well as tRNA maturation and turnover. Similarly, RNase II, encoded by the rnb gene, depolymerizes both mRNA and tRNA in a 3'→5' direction. While neither of the two genes is essential, disruption of both simultaneously is synthetically lethal. Thus, the present disclosure, in some embodiments, contemplates the protease-targeting of PNPase and RNase II.

Engineered Cells and Nucleic Acids

"Engineered cells" of the present disclosure are cells that comprise at least one engineered (e.g., recombinant or synthetic) nucleic acid, or are otherwise modified such that they are structurally and/or functionally distinct from their naturally-occurring counterparts. In some embodiments, an engineered cell comprises at least 1, at least 2, at least 3, at least 4, at least 5, at least 6, at least 7, at least 8, at least 9, or at least 10 engineered nucleic acids. In some embodiments, an engineered cell comprises 2 to 5, 2 to 10, or 2 to 20 engineered nucleic acids. In some embodiments, an engineered cell comprises 1, 2, 3, 4, 5, 6, 7, 8, 9, 10, 11, 12, 13, 14, 15, 16, 17, 18, 19, or 20 engineered nucleic acids. It should be understood that a cell that contains an engineered nucleic acid is considered an "engineered cell."

In some embodiments, a culture of "cells" or "engineered cells" contains a homogenous population or a heterogeneous population of cells. For example, a culture of cells may contain more than one type of cell, each type of cell expressing at least one engineered nucleic acid of the present disclosure.

The term "nucleic acid" refers to at least two nucleotides covalently linked together, and in some instances, may contain phosphodiester bonds (e.g., a phosphodiester "backbone"). Nucleic acids (e.g., components, or portions, of nucleic acids) may be naturally occurring or engineered. "Naturally occurring" nucleic acids are present in a cell that exists in nature in the absence of human intervention. "Engineered nucleic acids" include recombinant nucleic acids and synthetic nucleic acids. A "recombinant nucleic acid" refers to a molecule that is constructed by joining nucleic acid molecules (e.g., from the same species or from different species) and, typically, can replicate in a living cell. A "synthetic nucleic acid" refers to a molecule that is chemically or by other means synthesized or amplified, including those that are chemically or otherwise modified but can base pair with naturally occurring nucleic acid molecules. Recombinant and synthetic nucleic acids also include those molecules that result from the replication of either of the foregoing. It should be understood that engineered nucleic acids may contain portions of nucleic acids that are naturally occurring, but as a whole, engineered nucleic acids do not occur naturally and require human intervention. In some embodiments, a nucleic acid encoding a product of the present disclosure is a recombinant nucleic acid or a synthetic nucleic acid. In other embodiments, a nucleic acid encoding a product is naturally occurring.

An engineered nucleic acid encoding a product (e.g., a protein or nucleic acid), as provided herein, is operably linked to a "promoter," which is a control region of a nucleic acid at which initiation and rate of transcription of the remainder of a nucleic acid are controlled. A promoter drives expression or drives transcription of the nucleic acid that it regulates.

A promoter may be one naturally associated with a gene or sequence, as may be obtained by isolating the 5' non-coding sequences located upstream of the coding segment of a given gene or sequence. Such a promoter can be referred to as "endogenous."

In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR).

A promoter is considered to be "operably linked" when it is in a correct functional location and orientation in relation to the nucleic acid it regulates to control ("drive") transcriptional initiation and/or expression of that nucleic acid.

Engineered nucleic acids of the present disclosure may contain a constitutive promoter or an inducible promoter. A "constitutive promoter" refers to a promoter that is constantly active in a cell. An "inducible promoter" refers to a promoter that initiates or enhances transcriptional activity when in the presence of, influenced by, or contacted by an inducer or inducing agent. Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters, steroid-regulated promoters, metal-regulated promoters, pathogenesis-regulated promoters, temperature/heat-inducible, and light-regulated promoters.

An inducer or inducing agent may be endogenous or a normally exogenous condition (e.g., light), compound (e.g., chemical or non-chemical compound) or protein that contacts an inducible promoter in such a way as to be active in regulating transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter.

Engineered nucleic acids of the present disclosure may contain a transcriptional terminator. A "transcriptional terminator" is a nucleic acid sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated. The most commonly used type of terminator is a forward terminator. When placed downstream of a nucleic acid sequence that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only. In prokaryotic systems, terminators usually fall into two categories (1) rho-independent terminators and (2) rho-dependent terminators. Rho-independent terminators are generally composed of palindromic sequence that forms a stem loop rich in G-C base pairs followed by a string of uracil bases.

Terminators for use in accordance with the present disclosure include any terminator of transcription described herein or known to one of ordinary skill in the art. Non-limiting examples of terminators include the termination sequences of genes such as, for example, the bovine growth hormone terminator, and viral termination sequences such as, for example, the T0 terminator, the TE terminator, Lambda T1 and the T1T2 terminator found in bacterial systems. In some embodiments, the termination signal may be a sequence that cannot be transcribed or translated, such as those resulting from a sequence truncation.

Enzymes of the present disclosure may be encoded by nucleic acids that are located genomically (referred to as a "genomically-located nucleic acid") or are located episomally (referred to as an "episomally-located nucleic acid"). A nucleic acid that is located genomically in a cell is a nucleic acid that is located in the genome of the cell. A nucleic acid that is located episomally in a cell is a nucleic acid that is located on an autonomously-replicating episome in the cell, such as a plasmid. Genomically-located nucleic acids and episomally-located nucleic acids may be endogenous (e.g., originating from within the cell) to the cell or exogenous to the cell (e.g., originating from outside the cell). Typically, exogenous nucleic acids are engineered nucleic acids (e.g., recombinant or synthetic).

Engineered nucleic acids may be introduced into host cells using any means known in the art, including, without limitation, transformation, transfection (e.g., chemical (e.g., calcium phosphate, cationic polymers, or liposomes) or non-chemical (e.g., electroporation, sonoporation, impalefection, optical transfection, hydro dynamic)), and transduction (e.g., viral transduction).

Engineered cells, in some embodiments, express selectable markers. Selectable markers are typically used to select engineered cells that have taken up and expressed an engineered nucleic acid following transfection of the cell (or following other procedure used to introduce foreign nucleic acid into the cell). Thus, a nucleic acid encoding product may also encode a selectable marker. Examples of selectable markers include, without limitation, genes encoding proteins that increase or decrease either resistance or sensitivity to antibiotics (e.g., ampicillin resistance genes, kanamycin resistance genes, neomycin resistance genes, tetracycline resistance genes and chloramphenicol resistance genes) or other compounds. Other selectable markers may be used in accordance with the present disclosure.

An engineered cell "expresses" a product if the product, encoded by a nucleic acid (e.g., an engineered nucleic acid), is produced in the cell. It is well known in the art that gene expression refers to the process by which genetic instructions in the form of a nucleic acid are used to synthesize a product, such as a protein (e.g., an enzyme).

In some embodiments, proteins (e.g., nucleases) of the present disclosure may be engineered to contain a protease-recognition sequence and/or a periplasmic-targeting sequence, as provided herein.

Enzymes or other proteins encoded by a naturally-occurring nucleic acid may be referred to as "endogenous enzymes" or "endogenous proteins."

Engineered cells may be prokaryotic cells or eukaryotic cells. In some embodiments, engineered cells are bacterial cells, yeast cells, insect cells, mammalian cells, or other types of cells.

Engineered bacterial cells of the present disclosure include, without limitation, engineered *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., and *Pantoea* spp.

Engineered yeast cells of the present disclosure include, without limitation, engineered *Saccharomyces* spp., *Schizosaccharomyces*, *Hansenula*, *Candida*, *Kluyveromyces*, *Yarrowia* and *Pichia*.

In some embodiments, engineered cells of the present disclosure are engineered *Escherichia coli* cells, *Bacillus subtilis* cells, *Pseudomonas putida* cells, *Saccharomyces cerevisae* cells, or *Lactobacillus brevis* cells. In some embodiments, engineered cells of the present disclosure are engineered *Escherichia coli* cells.

Cell Culture

Typically, engineered cells are cultured. "Culturing" refers to the process by which cells are grown under controlled conditions, typically outside of their natural environment. For example, engineered cells, such as engineered bacterial cells, may be grown as a cell suspension in liquid nutrient broth, also referred to as liquid "culture medium."

Examples of commonly used bacterial *Escherichia coli* growth media include, without limitation, LB (Luria Bertani) Miller broth (1% NaCl): 1% peptone, 0.5% yeast extract, and 1% NaCl; LB (Luria Bertani) Lennox Broth (0.5% NaCl): 1% peptone, 0.5% yeast extract, and 0.5% NaCl; SOB medium (Super Optimal Broth): 2% peptone, 0.5% Yeast extract, 10 mM NaCl, 2.5 mM KCl, 10 mM MgCl2, 10 mM MgSO4; SOC medium (Super Optimal broth with Catabolic repressor): SOB+20 mM glucose; 2× YT broth (2× Yeast extract and Tryptone): 1.6% peptone, 1% yeast extract, and 0.5% NaCl; TB (Terrific Broth) medium: 1.2% peptone, 2.4% yeast extract, 72 mM K2HPO4, 17 mM KH2PO4 and 0.4% glycerol; and SB (Super Broth) medium: 3.2% peptone, 2% yeast extract, and 0.5% NaCl.

Examples of high density bacterial *Escherichia coli* growth media include DNAGro™ medium, ProGro™ medium, AutoX™ medium, DetoX™ medium, InduX™ medium, and SecPro™ medium.

In some embodiments, engineered cells are cultured under conditions that result in expression of products (e.g., proteins and/or nucleic acids). Such culture conditions may depend on the particular product being expressed and the desired amount of the product.

In some embodiments, engineered cells are cultured at a temperature of 30° C. to 40° C. For example, engineered cells may be cultured at a temperature of 30° C., 31° C., 32° C., 33° C., 34° C., 35° C., 36° C., 37° C., 38° C., 39° C. or 40° C. Typically, engineered cells, such as engineered bacterial cells, are cultured at a temperature of 37° C.

In some embodiments, engineered cells are cultured for a period of time of 12 hours to 72 hours, or more. For example, engineered cells may be cultured for a period of time of 12, 18, 24, 30, 36, 42, 48, 54, 60, 66, or 72 hours. Typically, engineered cells, such as engineered bacterial cells, are cultured for a period of time of 12 to 24 hours. In some embodiments, engineered cells are cultured for 12 to 24 hours at a temperature of 37° C.

In some embodiments, engineered cells are cultured (e.g., in liquid cell culture medium) to an optical density, measured at a wavelength of 600 nm (OD600), of 5 to 25. In some embodiments, engineered cells are cultured to an OD600 of 5, 10, 15, 20, or 25.

In some embodiments, engineered cells are cultured to a density of $1 \times 10^4$ to $1 \times 10^8$ viable cells/ml cell culture medium. In some embodiments, engineered cells are cultured to a density of $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, or $1 \times 10^8$ viable cells/ml. In some embodiments, engineered cells are cultured to a density of $2 \times 10^5$ to $3 \times 10^7$ viable cells/ml.

In some embodiments, engineered cells are cultured in a bioreactor. A bioreactor refers simply to a container in which cells are cultured, such as a culture flask, a dish, or a bag that may be single-use (disposable), autoclavable, or sterilizable. The bioreactor may be made of glass, or it may be polymer-based, or it may be made of other materials.

Examples of bioreactors include, without limitation, stirred tank (e.g., well mixed) bioreactors and tubular (e.g., plug flow) bioreactors, airlift bioreactors, membrane stirred tanks, spin filter stirred tanks, vibromixers, fluidized bed reactors, and membrane bioreactors. The mode of operating the bioreactor may be a batch or continuous processes and will depend on the engineered cells being cultured. A bioreactor is continuous when the feed and product streams are continuously being fed and withdrawn from the system. A batch bioreactor may have a continuous recirculating flow, but no continuous feeding of nutrient or product harvest. For intermittent-harvest and fedbatch (or batch fed) cultures, cells are inoculated at a lower viable cell density in a medium that is similar in composition to a batch medium. Cells are allowed to grow exponentially with essentially no external manipulation until nutrients are somewhat depleted and cells are approaching stationary growth phase. At this point, for an intermittent harvest batch-fed process, a portion of the cells and product may be harvested, and the removed culture medium is replenished with fresh medium. This process may be repeated several times. For production of recombinant proteins and antibodies, a fedbatch process may be used. While cells are growing exponentially, but nutrients are becoming depleted, concentrated feed medium (e.g., 10-15 times concentrated basal medium) is added either continuously or intermittently to supply additional nutrients, allowing for further increase in cell concentration and the length of the production phase. Fresh medium may be added proportionally to cell concentration without removal of culture medium (broth). To accommodate the addition of medium, a fedbatch culture is started in a volume much lower that the full capacity of the bioreactor (e.g., approximately 40% to 50% of the maximum volume).

Some methods of the present disclosure are directed to large-scale production of dsRNA. For large-scale production methods, engineered cells may be grown in liquid culture medium in a volume of 5 liters (L) to 50 L, or more. In some embodiments, engineered cells may be grown in liquid culture medium in a volume of greater than (or equal to) 10 L. In some embodiments, engineered cells are grown in liquid culture medium in a volume of 5 L, 10 L, 15 L, 20 L, 25 L, 30 L, 35 L, 40 L, 45 L, or 50 L, or more. In some embodiments, engineered cells may be grown in liquid culture medium in a volume of 5 L to 10 L, 5 L to 15 L, 5 L to 20 L, 5 L to 25 L, 5 L to 30 L, 5 L to 35 L, 5 L to 40 L, 5 L to 45 L, 10 L to 15 L, 10 L to 20 L, 10 L to 25 L, 20 L to 30 L, 10 L to 35 L, 10 L to 40 L, 10 L to 45 L, 10 L to 50 L, 15 L to 20 L, 15 L to 25 L, 15 L to 30 L, 15 L to 35 L, 15 L to 40 L, 15 L to 45 L, or 15 to 50 L.

Cell Lysates

Typically, culturing of engineered cells is followed by lysing the cells. "Lysing" refers to the process by which cells are broken down, for example, by viral, enzymatic, mechanical, or osmotic mechanisms. A "cell lysate" refers to a fluid containing the contents of lysed cells (e.g., lysed engineered cells), including, for example, organelles, membrane lipids, proteins, and nucleic acids. Cell lysates of the present disclosure may be produced by lysing any population of engineered cells, as provided herein.

Methods of cell lysis, referred to as "lysing," are known in the art, any of which may be used in accordance with the present disclosure. Such cell lysis methods include, without limitation, physical lysis and chemical (e.g., detergent-based) lysis.

Cell lysis can disturb carefully controlled cellular environments, resulting in protein degradation and modification by unregulated endogenous proteases and phosphatases. Thus, in some embodiments, protease inhibitors and/or phosphatase inhibitors may be added to lysis reagents, or these activities may be removed by gene inactivation or protease targeting.

Cell lysates, in some embodiments, may be combined with at least one nutrient. For example, cell lysates may be combined with $Na_2HPO_4$, $KH_2PO_4$, $NH_4Cl$, NaCl, $MgSO_4$, $CaCl_2$. Examples of other nutrients include, without limitation, magnesium sulfate, magnesium chloride, magnesium orotate, magnesium citrate, potassium phosphate monobasic, potassium phosphate dibasic, potassium phosphate tribasic, sodium phosphate monobasic, sodium phosphate dibasic, sodium phosphate tribasic, ammonium phosphate monobasic, ammonium phosphate dibasic, ammonium sulfate, ammonium chloride, ammonium hydroxide, Cell lysates, in some embodiments, may be combined with at least one cofactor. For example, cell lysates may be combined with adenosine diphosphate (ADP), adenosine triphosphate (ATP), nicotinamide adenine dinucleotide (NAD+), or other non-protein chemical compounds required for activity of an enzyme (e.g., inorganic ions and coenzymes).

In some embodiments, cell lysates are incubated under conditions that result in RNA depolymerization. In some embodiments, cell lysates are incubated under conditions that result in production of dsRNA.

Methods of the present disclosure include incubating a (at least one) cell lysate under conditions that result in RNA depolymerization and/or production of dsRNA. A cell lysate may be incubated at temperature of 4° C. to 45° C., or higher. For example, engineered cells may be incubated at a temperature of 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. In some embodiments, a cell lysate is incubated at a temperature of 4-6° C., 25° C., or 37° C. In some embodiments, a cell lysate is incubated at a temperature of 15° C. to 45° C.

In some embodiments, a cell lysate is incubated for a period of time of 30 minutes (min) to 48 hours (hr), or more. For example, engineered cells may be cultured for a period of time of 30 min, 45 min, 1 hr, 2 hrs, 3 hrs, 4 hrs, 5 hrs, 6 hrs, 7 hrs, 8 hrs, 9 hrs, 10 hrs, 11 hrs, 12 hrs, 18 hrs, 24 hrs, 30 hrs, 36 hrs, 42 hours, or 48 hours. In some embodiments, a cell lysate is incubated for a period of time of 2 hr to 48 hr. In some embodiments, a cell lysate is incubated for 24 hours at a temperature of 37° C.

The volume of cell lysate used for a single reaction may vary. In some embodiments, the volume of a cell lysate is 1 to 150 m$^3$. For example, the volume of a cell lysate may be 1 m$^3$, 5 m$^3$, 10 m$^3$, 15 m$^3$, 20 m$^3$, 25 m$^3$, 30 m$^3$, 35 m$^3$, 40 m$^3$, 45 m$^3$, 50 m$^3$, 55 m$^3$, 60 m$^3$, 65 m$^3$, 70 m$^3$, 75 m$^3$, 80 m$^3$, 85 m$^3$, 90 m$^3$, 95 m$^3$, 100 m$^3$, 105 m$^3$, 110 m$^3$, 115 m$^3$, 120 m$^3$, 125 m$^3$, 130 m$^3$, 135 m$^3$, 140 m$^3$, 145 m$^3$, or 150 m$^3$. In some embodiments, the volume of a cell lysate is 25 m$^3$ to 150 m$^3$, 50 m$^3$ to 150 m$^3$, or 100 m$^3$ to 150 m$^3$.

In some embodiments, a cell lysate or reaction mixture free of nuclease (e.g., ribonuclease) activity. A cell lysate or reaction mixture is considered "free of nuclease activity" if the cell lysate or reaction mixture is free of nucleases or if the amount of nuclease activity in the cell lysate or reaction is not detectable by standard assays used to detect protein (e.g., enzyme) activity. Non-limiting examples of enzymes assays include both continuous assays (e.g., spectrophotometric, fluorometric, calorimetric, chemiluminescent, light scattering, and microscale thermophoresis) and discontinuous assays (e.g., radiometric and chromatographic). Other enzymes assays are contemplated herein.

Protease Targeting

Engineered cells of the present disclosure may express (e.g., endogenously express) nuclease(s) necessary for RNA depolymerization that may, in turn, degrade a desired RNA product. To prevent, or reduce, degradation of RNA produced by the methods provided herein, endogenous and/or engineered nucleases can be modified to include a site-specific protease-recognition sequence in their protein sequence such that the nuclease may be "targeted" and cleaved for inactivation during RNA production (see, e.g., U.S. Publication No. 2012/0052547 A1, published on Mar. 1, 2012; and International Publication No. WO 2015/021058 A2, published Feb. 12, 2015, each of which is incorporated herein by reference). Nucleases that contain site-specific protease-recognition sequence are referred to as "protease-targeted nucleases." Cleavage of a protease-targeted nuclease results upon contact of the nuclease with a cognate site-specific protease in a cell lysate. Thus, engineered cells of a particular population may comprise an engineered nucleic acid encoding a protease-targeted nuclease, or other protease-targeted ribonuclease(s). Protease targeting of other enzymes is also contemplated herein.

As described in more detail below, protease-targeted nucleases (e.g., nucleases, or other ribonucleases, such as those described in Table 1, Table 6 and Table 7) of the present disclosure may also contain a periplasmic-targeting sequence. Sequestration of the protease-targeted nuclease to the periplasm during the cell growth phase prevents the nuclease from degrading cellular RNA required for cell growth.

In some embodiments, cells of the present disclosure contain an engineered nucleic acid encoding a cognate protease. In some embodiments, a cognate protease contains a periplasmic-targeting sequence, as discussed below. In some embodiments, cells of one population (e.g., of a first culture) contain an engineered nucleic acid encoding a protease-targeted nuclease, and cells of a different population (e.g., of a second culture) contain an engineered nucleic acid encoding a cognate protease that cleaves the protease-recognition sequence of the nuclease.

Examples of proteases that may be used in accordance with the present disclosure include, without limitation, alanine carboxypeptidase, Armillaria mellea, astacin, bacterial leucyl aminopeptidase, cancer procoagulant, cathepsin B, clostripain, cytosol alanyl aminopeptidase, elastase, endoproteinase Brg-C, enterokinase, gastricsin, gelatinase, Gly-X carboxypeptidase, glycyl endopeptidase, human rhinovirus 3C protease, hypodermin C, Iga-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2B, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin B, venombin BB and Xaa-pro aminopeptidase.

Periplasmic Targeting

In some embodiments, a nuclease (e.g., a ribonuclease) or other enzyme (e.g. protease) of an engineered cell contains a periplasmic-targeting sequence responsible for sequestering the nuclease or other enzyme to the periplasm of the cell. A "periplasmic-targeting sequence" is an amino acid sequence that targets to the periplasm of a cell the protein to which it is linked. A protein that is linked to a periplasmic-targeting sequence will be sequestered in the periplasm of the cell in which the protein is expressed.

Periplasmic-targeting sequences may be derived from the N-terminus of bacterial secretory protein, for example. The sequences vary in length from about 15 to about 70 amino acids. The primary amino acid sequences of periplasmic-targeting sequences vary, but generally have a common structure, including the following components: (i) the N-terminal part has a variable length and generally carries a net positive charge; (ii) following is a central hydrophobic core of about 6 to about 15 amino acids; and (iii) the final component includes four to six amino acids which define the cleavage site for signal peptidases.

Periplasmic-targeting sequences of the present disclosure, in some embodiments, may be derived from a protein that is secreted in a Gram negative bacterium. The secreted protein may be encoded by the bacterium, or by a bacteriophage that infects the bacterium. Examples of Gram negative bacterial sources of secreted proteins include, without limitation, members of the genera *Escherichia, Pseudomonas, Klebsiella, Salmonella, Caulobacter, Methylomonas, Acetobacter, Achromobacter, Acinetobacter, Aeromonas, Agrobacterium, Alcaligenes, Azotobacter, Burkholderia, Citrobacter, Comamonas, Enterobacter, Erwinia, Rhizobium, Vibrio,* and *Xanthomonas.*

Examples of periplasmic-targeting sequences for use in accordance with the present disclosure include, without limitation, sequences selected from the group consisting of:

```
                                        (SEQ ID NO: 1)
MKIKTGARILALSALTTMMFSASALA;

(SEQ ID NO: 2)
MKQSTIALALLPLLFTPVTKA;

(SEQ ID NO: 3)
MMITLRKLPLAVAVAAGVMSAQAMA;

(SEQ ID NO: 4)
MNKKVLTLSAVMASMLFGAAAHA;

(SEQ ID NO: 5)
MKYLLPTAAAGLLLLAAQPAMA;

(SEQ ID NO: 6)
MKKIWLALAGLVLAFSASA;

(SEQ ID NO: 7)
MMTKIKLLMLIIFYLIISASAHA;

(SEQ ID NO: 8)
MKQALRVAFGFLILWASVLHA;

(SEQ ID NO: 9)
MRVLLFLLLSLFMLPAFS;
and (SEQ ID NO: 10)
MANNDLFQASRRRFLAQLGGLTVAGMLGPSLLTPRRATA.
```

EXAMPLES

Engineered cells of a first population express a protease-targeted nuclease, including, but not limited to those listed in Table 1, which is localized to the periplasm. Engineered cells of a second population express at least one NMP and/or NDP kinase, a DNA-dependent RNA polymerase and/or a RNA-dependent RNA polymerase, and a site-specific protease localized to the periplasm. Additionally, cells of the second population contain a DNA template encoding a dsRNA of interest, wherein the DNA template is flanked by genetic elements (e.g., 5' promoter, 3' terminator) that regulate transcription of the DNA template. Cells of each population are engineered to contain inactivated or protease-targeted RNases, including, but not limited to, those listed in Table 6 and Table 7, or chromosomal deletions of genes encoding such RNases.

Cells of the first population are grown to a high cell density using conventional fermentation means with glucose and/or other sugars or carbon-based molecules serving as the carbon and energy source. Upon reaching an appropriate cell density, expression of the nuclease is induced through either the addition of an inducer molecule or through other means. Protein induction is allowed to continue until a sufficient level of protein expression is reached. Following growth and induction, the biomass is concentrated, where necessary. The biomass is subsequently lysed, allowing access of the nuclease to the cellular oligomeric RNA molecules. This material is incubated, preferentially at 37° C., until appropriate RNA depolymerization has occurred (e.g., 2 hours to 24 hours).

Cells of the second population are grown, induced and concentrated in a manner similar to the cells of the first population. The resulting biomass is lysed and mixed with the lysate from cells of the first population. Mixing of the cellular lysates allows for proteolytic inactivation of the nuclease expressed in cells of the first population as well as the various targeted RNases from both cells populations. The monomeric NMPs and/or NDPs yielded from the nuclease-mediated depolymerization of oligomeric RNA in cells of the first population are subsequently converted to NTPs through the activity of at least one of the nucleotide kinases listed in Table 2 and Table 3. Polyphosphate is added to the reaction to generate the required ATP for phosphorylation of the NMPs and NDPs via polyphosphate kinase. The resulting NTPs are oligomerized via the action of either the DNA-dependent RNA polymerase and/or RNA-dependent RNA polymerase using the aforementioned extrachromosomal DNA molecule as template yielding the desired, sequence-specific dsRNA molecule.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

---

What is claimed is:

1. A method of producing a cell lysate for use in cell-free production of ribonucleic acid (RNA), the method comprising:
   (a) culturing bacterial cells having a periplasmic space to a desired cell density, wherein the cells comprise at least one engineered nucleic acid containing a promoter operably linked to a sequence encoding a nuclease that includes a protease-recognition site and a periplasmic-targeting sequence, wherein at least one endogenous ribonuclease is genetically inactivated or inactivated via targeted proteolysis in the cells, and wherein the nuclease is sequestered in the periplasm following its expression;
   (b) lysing the cells produced in step (a), thereby producing a first cell lysate, and
   (c) incubating the first cell lysate, thereby producing a first cell lysate containing nucleotide 5'-monophosphates.

2. The method of claim 1, wherein the promoter operably linked to a sequence encoding a nuclease is inducible.

3. The method of claim 1, further comprising producing a second cell lysate according to:
   (d) culturing bacterial cells having a periplasmic space to a desired cell density, wherein the cells comprise (i) at least one engineered nucleic acid containing a promoter operably linked to a sequence encoding a cognate protease that cleaves the protease-recognition site of the nuclease, wherein the cognate protease comprises a periplasmic-targeting sequence and (ii) at least one engineered nucleic acid containing a promoter operably linked to a sequence encoding a nucleotide kinase, wherein at least one endogenous ribonuclease is genetically inactivated or inactivated via targeted proteolysis in the cells; and (e) lysing the cultured cells produced in step (d), thereby producing a second cell lysate.

4. The method of claim 1, wherein the nuclease is selected from the group consisting of S1 Nuclease, NucA, PNPase, RNase II, RNase III, and RNase R.

5. The method of claim 1, wherein the cells contain at least one endogenous ribonuclease comprising a protease-recognition site and/or at least one chromosomal deletion in a gene encoding an endogenous ribonuclease.

6. The method of claim 5, wherein at least one endogenous ribonuclease is selected from the group consisting of RNase III, RNase I, RNaseR, PNPase, RNase II, RNase T, RNase E and combinations thereof.

7. The method of claim 3, wherein the nucleotide kinase is a nucleotide monophosphate kinase or a nucleotide diphosphate kinase.

8. The method of claim 7, wherein the nucleotide monophosphate kinase is selected from the group consisting of uridylate kinase, cytidylate kinase, guanylate kinase, and adenylate kinase.

9. The method of claim 1, wherein at least one endogenous enzyme that degrades polyphosphate is genetically inactivated in the cells or inactivated via targeted proteolysis in the cells.

10. The method of claim 9, wherein at least one of the endogenous enzyme(s) that degrades polyphosphate is selected from the group consisting of nucleoside monophosphatase, nucleoside diphosphatase, nucleoside triphosphatase, nucleoside triphosphate phosphohydrolase, and exopolyphosphatase.

11. The method of claim 3, wherein the cells of step (d) further comprise (iii) at least one engineered nucleic acid containing a promoter operably linked to a sequence encoding an RNA polymerase and/or (iv) an engineered deoxyribonucleic acid (DNA) template containing a promoter operably linked to a sequence encoding an RNA.

12. The method of claim 11, wherein the engineered DNA template is located on an expression vector containing an endonuclease cleavage site.

13. The method of claim 12, wherein the endonuclease cleavage site is an I-SceI endonuclease cleavage site.

14. The method of claim 3 further comprising:

(f) combining the first cell lysate produced in step (b), the second cell lysate produced in step (e), at least one RNA polymerase, an engineered deoxyribonucleic acid (DNA) template containing a promoter operably linked to a sequence encoding an RNA, and polyphosphate; and (g) incubating the mixture, thereby producing the RNA.

15. The method of claim 1, wherein the method comprises producing a cell lysate for use in cell-free production of double-stranded RNA (dsRNA).

16. A cell-free method of producing a ribonucleic acid (RNA) of interest, the method comprising:

(a) combining a first cell lysate with a second cell lysate, wherein
the first cell lysate comprises (i) a nuclease that includes a protease-recognition site and a periplasmic-targeting sequence, and (ii) nucleotide 5'-monophosphates, and
the second cell lysate comprises (iii) a cognate protease that cleaves the protease-recognition site of the nuclease and (iv) a nucleotide kinase, thereby forming a reaction mixture; and (b) incubating the reaction mixture with an RNA polymerase, an engineered deoxyribonucleic acid (DNA) template containing a promoter operably linked to a sequence encoding an RNA of interest, and polyphosphate, thereby producing the RNA of interest.

17. The method of claim 3, wherein the nuclease is selected from the group consisting of S1 Nuclease, NucA, PNPase, RNase II, RNase III, and RNase R.

18. The method of claim 3, wherein at least one endogenous enzyme that degrades polyphosphate is genetically inactivated in the cells.

19. The method of claim 1, wherein the bacterial cells are *E. coli* cells.

20. The method of claim 1, further comprising:

(d) adding a cognate protease that cleaves the protease-recognition site of the nuclease after the first cell lysate containing nucleotide 5'-monophosphates is produced.

21. The method of claim 7, wherein the nucleotide diphosphate kinase is selected from the group consisting of nucleoside phosphate kinase, pyruvate kinase, and polyphosphate kinase.

22. The method of claim 11, wherein (iii) comprises an engineered nucleic acid encoding a DNA-dependent RNA polymerase and an engineered nucleic acid encoding an RNA-dependent RNA polymerase.

23. The method of claim 22, wherein the DNA-dependent RNA polymerase is T7 RNA polymerase.

24. The method of claim 11 further comprising:

(f) combining the first cell lysate produced in step (b), the second cell lysate produced in step (e), and polyphosphate; and (g) incubating the mixture, thereby producing the RNA.

* * * * *

SEQUENCE LISTING

<160> NUMBER OF SEQ ID NOS: 10

<210> SEQ ID NO 1
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 1

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 2
<211> LENGTH: 21
<212> TYPE: PRT
<213> ORGANISM: Artificial Sequence

```
<220> FEATURE:
<223> OTHER INFORMATION: Synthetic Polypeptide

<400> SEQUENCE: 2

Met Lys Gln Ser Thr Ile Ala Leu Ala Leu Leu Pro Leu Leu Phe Thr
1               5                   10                  15

Pro Val Thr Lys Ala
            20

<210> SEQ ID NO 3
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 3

Met Met Ile Thr Leu Arg Lys Leu Pro Leu Ala Val Ala Val Ala Ala
1               5                   10                  15

Gly Val Met Ser Ala Gln Ala Met Ala
            20                  25

<210> SEQ ID NO 4
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 4

Met Asn Lys Lys Val Leu Thr Leu Ser Ala Val Met Ala Ser Met Leu
1               5                   10                  15

Phe Gly Ala Ala Ala His Ala
            20

<210> SEQ ID NO 5
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 5

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 6
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 6

Met Lys Lys Ile Trp Leu Ala Leu Ala Gly Leu Val Leu Ala Phe Ser
1               5                   10                  15

Ala Ser Ala

<210> SEQ ID NO 7
<211> LENGTH: 23
<212> TYPE: PRT
<213> ORGANISM: Artificial Sequence
```

```
<220> FEATURE:
<223> OTHER INFORMATION: Synthetic Polypeptide

<400> SEQUENCE: 7

Met Met Thr Lys Ile Lys Leu Leu Met Leu Ile Ile Phe Tyr Leu Ile
1               5                   10                  15

Ile Ser Ala Ser Ala His Ala
            20

<210> SEQ ID NO 8
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 8

Met Lys Gln Ala Leu Arg Val Ala Phe Gly Phe Leu Ile Leu Trp Ala
1               5                   10                  15

Ser Val Leu His Ala
            20

<210> SEQ ID NO 9
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 9

Met Arg Val Leu Leu Phe Leu Leu Leu Ser Leu Phe Met Leu Pro Ala
1               5                   10                  15

Phe Ser

<210> SEQ ID NO 10
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 10

Met Ala Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala
            35
```